(12) United States Patent
Yoshida et al.

(10) Patent No.: US 9,907,510 B2
(45) Date of Patent: Mar. 6, 2018

(54) ELECTRONIC APPARATUS THAT CONTROLS PRESS STATE BETWEEN USER AND BIOSENSOR, CONTROL METHOD, AND STORAGE MEDIUM

(71) Applicant: CASIO COMPUTER CO., LTD., Tokyo (JP)

(72) Inventors: Kaoru Yoshida, Tokyo (JP); Keiichi Imamura, Tokyo (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 0 days.

(21) Appl. No.: 15/044,617

(22) Filed: Feb. 16, 2016

(65) Prior Publication Data

US 2016/0235364 A1      Aug. 18, 2016

(30) Foreign Application Priority Data

Feb. 17, 2015   (JP) .................................. 2015-028722
Sep. 30, 2015   (JP) .................................. 2015-193572

(51) Int. Cl.
*A61B 5/024*        (2006.01)
*H01L 41/04*        (2006.01)
*A61B 5/026*        (2006.01)
*A61B 5/00*         (2006.01)

(52) U.S. Cl.
CPC ............ *A61B 5/681* (2013.01); *A61B 5/0059* (2013.01); *A61B 5/02416* (2013.01); *A61B 5/6843* (2013.01)

(58) Field of Classification Search
CPC ......... A61B 5/02; A61B 5/0245; A61B 5/681; A61B 5/0059; A61B 5/6843; A61B 5/02416
USPC ......................................... 600/324, 479, 509
See application file for complete search history.

(56) References Cited

U.S. PATENT DOCUMENTS

2015/0335283 A1*  11/2015  Fish .................... A61B 5/02416
                                                   600/324

FOREIGN PATENT DOCUMENTS

JP         2013-31597 A      2/2013

* cited by examiner

*Primary Examiner* — Carl H Layno
*Assistant Examiner* — Jon Eric C Morales
(74) *Attorney, Agent, or Firm* — Fitch Even Tabin & Flannery LLP

(57) ABSTRACT

To improve convenience in a wearable electronic apparatus that measures biological information. An electronic apparatus includes a sensor mechanism, a main body, and a retaining mechanism. The sensor mechanism acquires biological information of a user. The main body supports the sensor mechanism in a movable manner in an upper/lower direction. The retaining mechanism changes the sensor mechanism and the user's body between an unpress state and a press state by moving the sensor mechanism at the main body. With the electronic apparatus, a displacement of the sensor mechanism from the body is prevented and the maintenance of a contact condition is secured, an optical measurement becomes possible; therefore, it is thereby possible to improve convenience for a user without adjusting a position, etc.

21 Claims, 18 Drawing Sheets

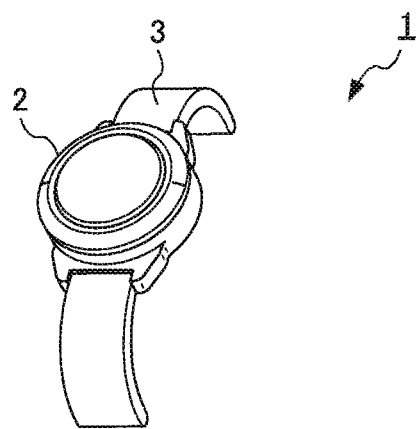
FIG. 1
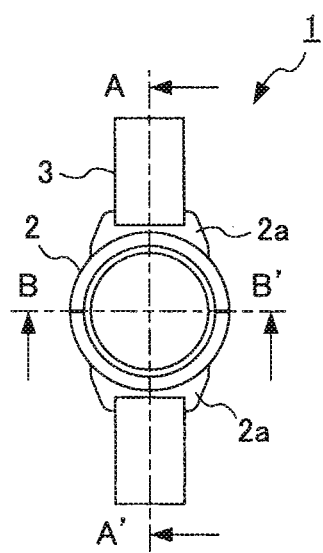 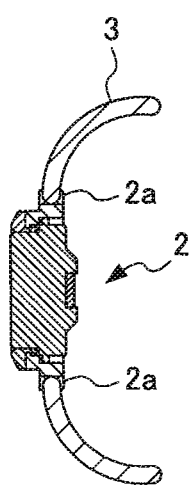 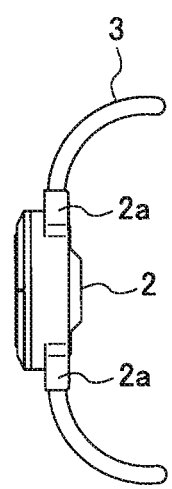
FIG. 2A  FIG. 2B  FIG. 2C
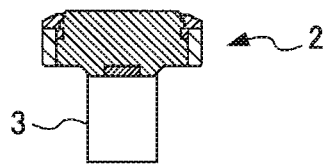
FIG. 2D

FIG. 20A  [DETECTING HIGH PRESSURE]

FIG. 20B  [DETECTING LOW PRESSURE]

FIG. 20C  [PRESSURE IS NOT DETECTED]

ELECTRONIC APPARATUS THAT CONTROLS PRESS STATE BETWEEN USER AND BIOSENSOR, CONTROL METHOD, AND STORAGE MEDIUM

This application is based upon and claims the benefit of priority under 35 USC 119 of Japanese Patent Application No. 2015-028722 filed on Feb. 17, 2015 and Japanese Patent Application No. 2015-193572 filed on Sep. 30, 2015 the entire disclosure of which, including the description, claims, drawings, and abstract, is incorporated herein by reference in its entirety.

BACKGROUND OF THE INVENTION

Related Art

Conventionally, as disclosed in Japanese Unexamined Patent Application, Publication No. 2013-031597, a wrist-type electronic apparatus has been known which includes a sensor for measuring biological information on the side of the living body. For such an electronic apparatus, methods such as tightly fastening a band for wearing by wrapping around an arm or using an elastic band are used in order to fit an electronic apparatus main body to the living body.

Furthermore, Japanese Unexamined Patent Application, Publication No. 2013-031597 also discloses a biological information measurement apparatus including a structure that movably supports an inner shell having a sensor in a vertical direction with respect to a sensor face by an outer shell.

SUMMARY OF THE INVENTION

An electronic apparatus includes: a sensor unit that acquires biological information of a user; an outer case that supports the sensor unit in a movable manner in an upper/lower direction; and a pressing portion that changes the sensor unit and a body of the user between an unpress state and a press state by moving the sensor unit. A control method executed by an electronic apparatus including: a sensor unit that acquires biological information of a user; an outer case that supports the sensor unit in a movable manner in an upper/lower direction; and a pressing portion that changes the sensor unit and a body of the user between an unpress state and a press state by moving the sensor unit, includes: a control step of changing a pressed state between a body of a user and the sensor unit by controlling the pressing portion. A non-transitory storage medium encoded with a computer-readable program enables a computer which controls an electronic apparatus including: a sensor unit that acquires biological information of a user; an outer case that supports the sensor unit in a movable manner in an upper/lower direction; and a pressing portion that changes the sensor unit and a body of the user between an unpress state and a press state by moving the sensor unit, to execute functions as: a control unit that changes a pressed state between a body of a user and the sensor unit by controlling the pressing portion.

BRIEF DESCRIPTION OF THE DRAWINGS

FIG. 1 is a perspective view showing an outer appearance of an electronic apparatus according to an embodiment of the present invention;

FIG. 2A is a front elevation view showing a structure of an electronic apparatus according to one embodiment of the present invention;

FIG. 2B is a cross-sectional view along the line A-A' showing a structure of an electronic apparatus according to one embodiment of the present invention;

FIG. 2C is a side view from the right showing a structure of an electronic apparatus according to one embodiment of the present invention;

FIG. 2D is a cross-sectional view along the line B-B' showing a structure of an electronic apparatus according to one embodiment of the present invention;

FIG. 20A is a schematic view illustrating a method of judging a pressure level;

FIG. 20B is a schematic view illustrating a method of judging a pressure level;

FIG. 20C is a schematic view illustrating a method of judging a pressure level;

DETAILED DESCRIPTION OF THE INVENTION

Embodiments of the present invention are explained below with reference to the drawings.

First Embodiment

[Configuration]

FIG. 1 is a perspective view showing an outer appearance of an electronic apparatus according to one embodiment of the present invention.

Furthermore, FIG. 2 is a view showing a structure of the electronic apparatus 1 according to one embodiment of the present invention.

FIG. 2A is a front elevation view, FIG. 2B is a cross-sectional view along the line A-A', FIG. 2C is a side view from the right, and FIG. 2D is a cross-sectional view along the line B-B'.

The electronic apparatus 1 is configured as, for example, a wrist-type electronic apparatus worn on a wrist.

As shown in FIGS. 1 and 2, the electronic apparatus 1 includes a main body 2 and a band 3.

The main body 2 includes support parts 2a that support the band 3 at the upper end position and the lower end position in the front elevation view of FIG. 2A.

FIG. 3 is an exploded view showing a structure of the main body 2.

Figure 3A:
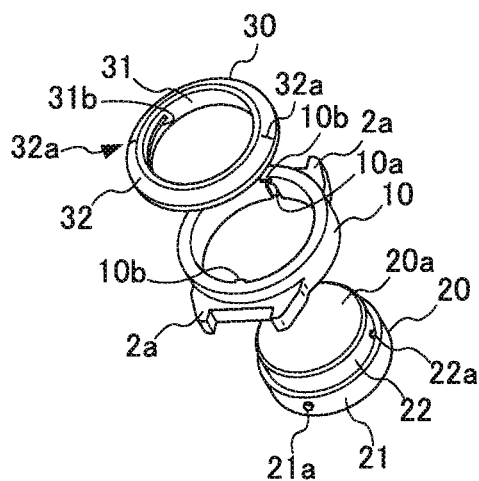
FIG. 3A is an exploded view showing a structure of a main body and a perspective view seen from the front elevation side.
Figure 3B:
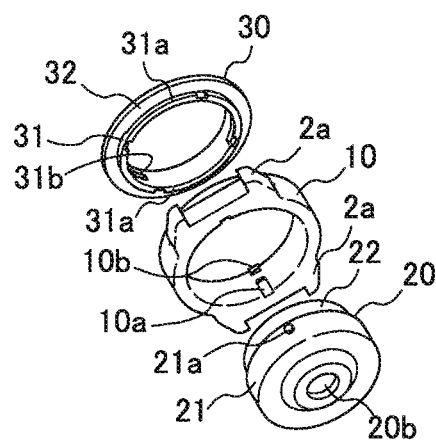
FIG. 3B is an exploded view showing a structure of a main body and a perspective view seen from the back face side.

FIG. 3A is a perspective view seen from the front elevation side, and FIG. 3B is a perspective view seen from the back face side.

Furthermore, FIG. 4 is a view showing a structure of a main body 2.

Figure 4A:
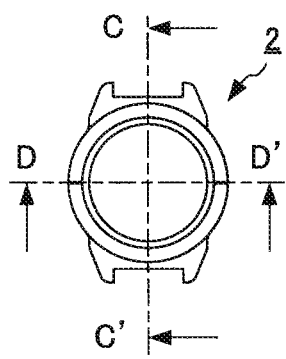
FIG. 4A is a front elevation view of a main body.
Figure 4B:
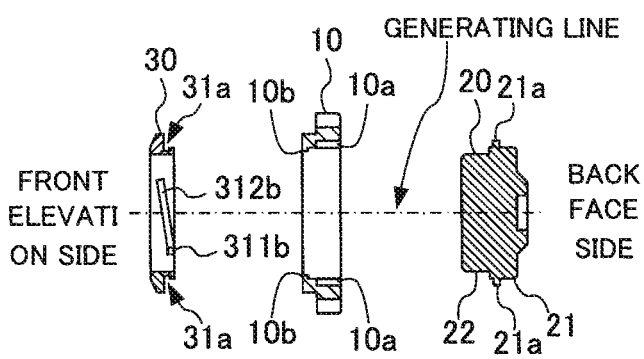
FIG. 4B is a cross-sectional view of the main body along the line C-C'.
Figure 4C:
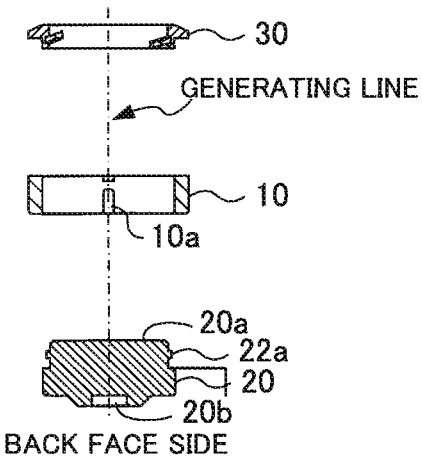
FIG. 4C is a cross-sectional view of the main body along the line D-D'.

FIG. 4A is a front elevation view of the main body 2, FIG. 4B is a cross-sectional view of the main body 2 along the line C-C', and FIG. 4C is a cross-sectional view of the main body 2 along the line D-D'.

As shown in FIGS. 3 and 4, the main body 2 includes an outer case 10, an inner case 20, and a rotating body 30 (pressing member, pressurized-attaching member).

The main body 2 has a configuration in which the inner case 20 and the rotating body 30 are assembled to the outer case 10.

The outer case 10 is a substantially cylindrical member constituting a frame body of the main body 2.

The outer case 10 includes the support parts 2a that support the band 3 at two locations which are 180 degrees away from each other on the circumferential face with respect to the central axis with the intersection of the lines A-A' and B-B' as its center.

Furthermore, a first boss receiving groove 10a and an outer case guide 10b are provided at the inner circumferential face of the outer case 10.

The first boss receiving groove 10a has a width corresponding to the diameter of a first boss 21a (described later) and extends in a direction along a generating line showed in FIG. 4B from the end of the back face side at the inner circumferential face.

As described later, the length of the first boss receiving groove 10a in the direction of the generating line is set so as to correspond to a distance of the inner case 20 moving in an axial direction (in a direction of a vertical line with the back face side in the direction of gravitational force) with respect to the outer case 10 by way of the rotation of the rotating body 30.

The first boss receiving groove 10a is provided at two locations which are 180 degrees away from each other with respect to the central axis of the outer case 10.

The outer case guide 10b projects in a hook shape from the inner circumferential face of the outer case 10 and supports in a rotatable manner the rotating body 30 by engaging with a rotating body guide groove 31a (described later).

The outer case guide 10b is provided at two locations which are 180 degrees away from each other with respect to the central axis of the outer case 10.

In the present embodiment, the outer case guide 10b is provided at the end of the front elevation side at a location at which the first boss receiving groove 10a is provided.

The inner case 20 includes a processor that controls the electronic apparatus 1, a storage unit such as ROM (Read Only Memory) or RAM (Random Access Memory), a battery, etc.

Furthermore, a display 20a displaying information is provided at the front elevation side of the inner case 20, and a sensor 20b that detects biological information (such as pulsation, blood pressure, body temperature, etc.) is provided at the back face side of the inner case 20.

The inner case 20 is a substantially column-shaped member.

The inner case 20 includes a large diameter part 21 having a diameter corresponding to the inner circumferential face of the outer case 10 and a small diameter part 22 having a diameter which is smaller than the diameter of the large diameter part 21 and corresponds to the inner circumferential face of the rotating body 30.

The large diameter part 21 includes the first boss 21a that engages with the first boss receiving groove 10a at two locations which are 180 degrees away from each other with respect to the central axis on the outer circumferential face.

The first boss 21a is a column-shaped projection that projects from the outer circumferential face of the large diameter part 21.

Since the first boss 21a can move in the direction of the generating line within the first boss receiving groove 10a, as described later, the inner case 20 can move in the axial direction with respect to the outer case 10 by way of the rotation of the rotating body 30.

Furthermore, the sensor 20b that detects biological information is provided at the back face side of the large diameter part 21.

The sensor 20b can perform detection with higher precision by being pressed (pressurized-attached) to a user's body when detecting biological information.

The small diameter part 22 includes a second boss 22a that engages with the second boss receiving groove 31b at two locations of the outer circumferential face which are 180 degrees away from the central axis.

The second boss 22a is a column-shaped projection that projects from the outer circumferential face of the small diameter part 22.

It should be noted that the radius from the central axis of the inner case 20 to the tip end of the second boss 22a is set so as not to exceed the radius of the outer circumferential face of the large diameter part 21.

Since the second boss 22a can move along the second boss receiving groove 31b which is provided to be oblique with respect to the generating line, as described later, the inner case 20 moves in the axial direction with respect to the rotating body 30 by way of the rotation of the rotating body 30.

It should be noted that, in the present embodiment, the first boss 21a and the second boss 22a are provided at locations 90 degrees away from each other with respect to the central axis.

Furthermore, the display 20a is provided at the front elevation side of the small diameter part 22 which displays a variety of information such as a detected result from the sensor 20b, time, etc.

The rotating body 30 is provided at the front elevation side of the outer case 10.

The rotating body 30 constitutes a frame body which surrounds the display 20a in a state of the inner case 20 being provided within the outer case 10.

Furthermore, the rotating body 30 can rotate with the central axis as its center, and rotates without moving in the axial direction with respect to the outer case 10 while moving the inner case 20 in the axial direction corresponding to the rotation.

More specifically, the rotating body 30 includes an inner cylindrical part 31 inserted into the outer case 10 and a circular frame part 32 arranged at the front elevation side of the outer case 10.

Figure 5:
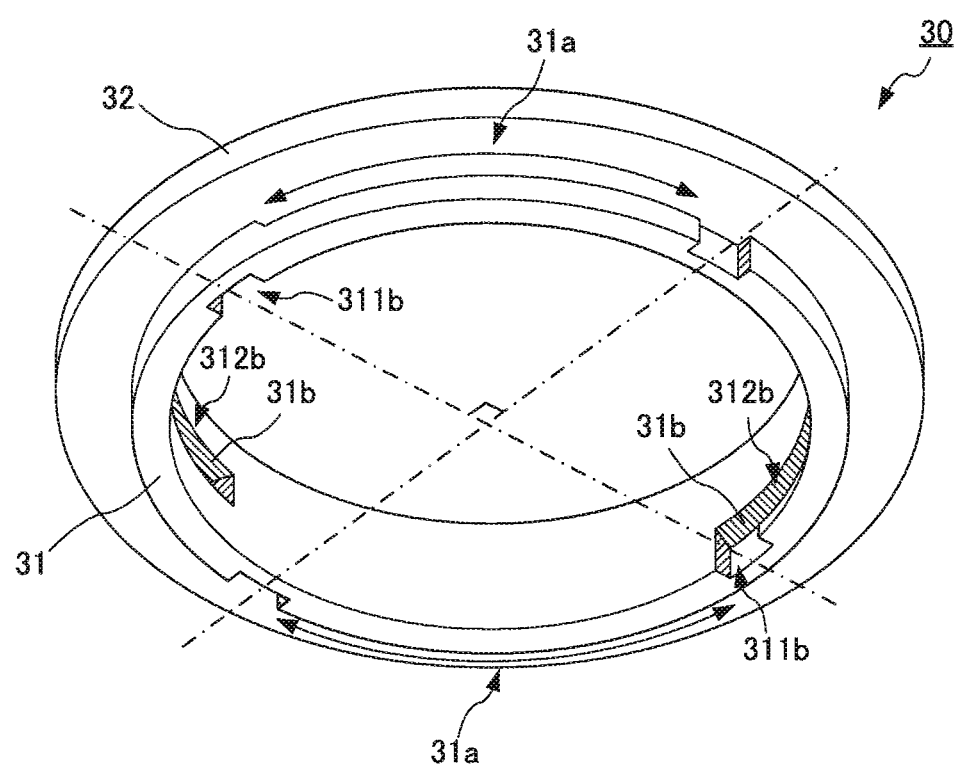
FIG. 5 is a perspective view showing a structure of a rotating body.

FIG. 5 is a perspective view showing a structure of the rotating body 30.

It should be noted that FIG. 5 shows a perspective view from the back face side.

As shown in FIG. 5, the inner cylindrical part 31 has a substantially cylindrically shaped structure including an outer circumferential face corresponding to the inner circumferential face of the outer case 10.

The inner cylindrical part 31 includes the rotating body guide groove 31a that engages with the outer case guide 10b at two locations of the outer circumferential face that are 180 degrees away from each other with respect to the central axis.

The rotating body guide grooves 31a at the two locations are provided along a circle (i.e. along a circumferential direction of the outer circumferential face) which intersects with a plane at which the outer circumferential face of the inner cylindrical part 31 is perpendicular to the central axis.

In other words, when the rotating body 30 rotates, the rotating body guide groove 31a engages the outer case guide 10b without moving in the axial direction.

In the present embodiment, each of the rotating body guide grooves 31a is provided in a range of 90 degrees with respect to the central axis.

It should be noted that the range in which the rotating body guide groove 31a is provided is set so as to correspond to the length of the second boss receiving groove 31b (described later).

Furthermore, the inner cylindrical part 31 includes the second boss receiving groove 31b that engages with the second boss 22a at two locations of the inner circumferential face which are 180 degrees away from each other with respect to the central axis.

The second boss receiving groove 31b has a configuration which, at an inner circumferential face of the inner cylindrical part 31, includes a straight part 311b that extends in the direction of the generating line from the end of the back face side to a bending point, and an oblique part 312b that is bent from the straight part 311b and extends in the circumferential direction (i.e., oblique with respect to the generating line) up to a terminal position in the middle of the inner circumferential face as approaching the end on the front elevation side.

Therefore, when the second boss 22a becomes engaged with the second boss receiving groove 31b, the rotating body 30 rotates after the second boss 22a passing the straight part 311b abuts the position of the bending point.

Due to this rotation, the second boss 22a can move in the range from the bending point to the terminal position of the oblique part 312b in the second boss receiving groove 31b.

With such a configuration, in conjunction with the rotating body 30 rotating, the inner case 20 moves to the front elevation side or the back face side along the central axis.

The length in the direction of the central axis of the straight part 311b and the oblique part 312b (i.e. the second boss receiving groove 31b) of the rotating body 30 (i.e. the distance of the second boss 22a moving in the direction of the central axis) is a length corresponding to the length in the direction of the central axis of the first boss receiving groove 10a of the outer case 10 (the distance of the first boss 21a moving in the direction of the central axis).

Therefore, when the rotating body 30 rotates in a state of the second boss 22a being engaged at the position of the bending point, the second boss 22a moves from the straight part 311b (bending point) to the oblique part 312b.

At the same time, the first boss 21a can move the first boss receiving groove 10a and, in conjunction with the rotating body 30 rotating, the inner case 20 moves to the front elevation side or the back face side along the central axis.

The frame part 32 is configured to be provided at the front elevation side of the inner cylindrical part 31 and integrally connected with the inner circumferential face of the inner cylindrical part 31.

Furthermore, the frame part 32 is configured as a circular member having a predetermined width in a direction of the radius expanding from the central axis.

The radius of the frame part 32 is set so that the outer circumference of the frame part 32 corresponds to the radius of the outer circumferential face of the outer case 10.

Marks 32a indicating rotating positions of the frame part 32 are provided at positions which are 180 degrees away from each other with respect to the central axis at the front elevation side of the frame part 32.

Next, the relational change between members when rotating the rotating body 30 will be explained.

Figure 6A:
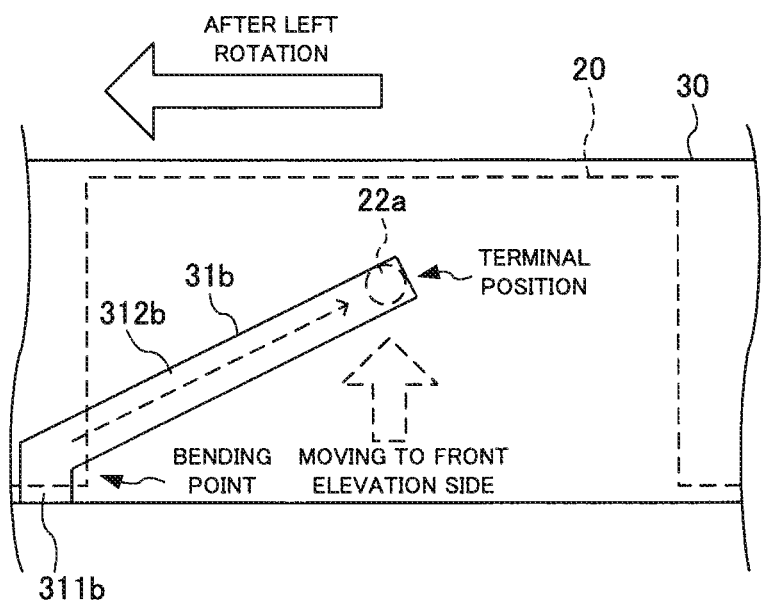
FIG. 6A is a schematic view showing a change of a positional relationship between an inner circumferential face of a rotating body and an inner case including a second boss.
Figure 6B:
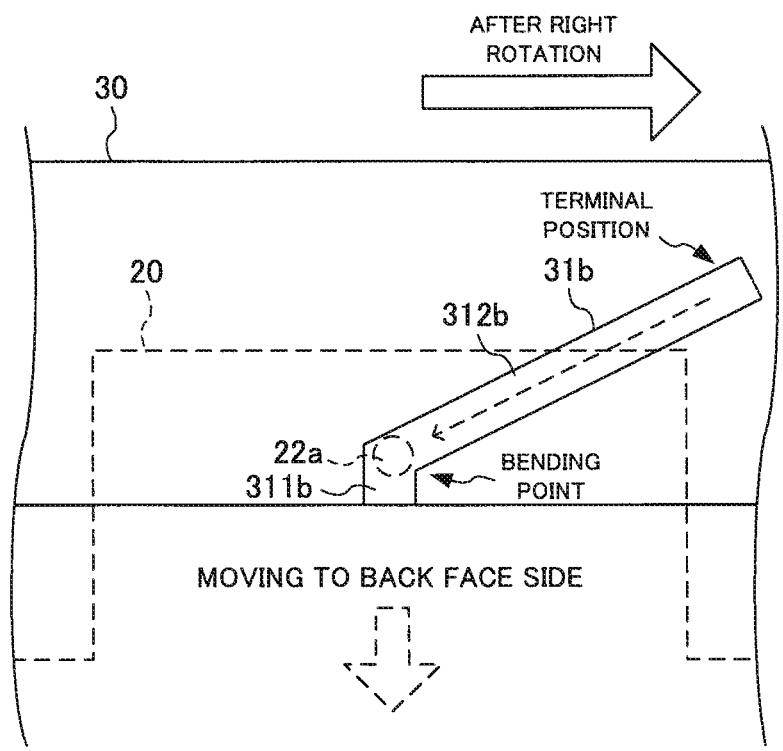
FIG. 6B is a schematic view showing a change of a positional relationship between an inner circumferential face of a rotating body and an inner case including a second boss and shows a case in which the second boss is located at a bending point of the second boss receiving groove.

FIG. 6 is a schematic view showing a change of the positional relationship between the inner circumferential face of the rotating body 30 and the inner case 20 including the second boss 22a. FIG. 6A shows a case in which the second boss 22a is located at a terminal position of the second boss receiving groove 31b. FIG. 6B shows a case in which the second boss 22a is located at a bending point of the second boss receiving groove 31b.

Furthermore, FIG. 7 is a fragmentary sectional view showing a change of the engaging relationship between members schematically. More specifically, in FIG. 7, fragments of cross-sectional views along the lines A-A' and B-B' of FIG. 2 in the cases of the inner case 20 being located at the front elevation side and the back face side are enlarged and shown schematically, respectively.

As described above, in the electronic apparatus 1, the first boss 21a of the inner case 20 is engaged with the first boss receiving groove 10a of the outer case 10, the second boss 22a of the inner case 20 is engaged with the second boss receiving groove 31b of the rotating body 30, and the outer case guide 10b of the outer case 10 is engaged with the rotating body guide groove 31a of the rotating body 30.

Figure 7A:
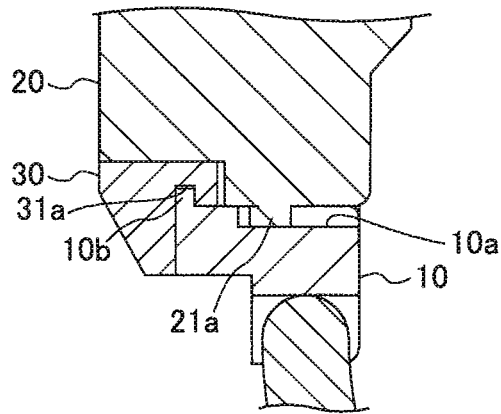
FIG. 7A is a fragmentary sectional view showing a change of an engaging relationship between members schematically and a view showing a fragment of a cross-sectional view along the line A-A' in a case of an inner case being located at a front elevation side.

Then, in the case of the rotating body 30 being rotated to the left when viewed from the front, as shown in FIG. 7A, since the rotating body guide groove 31a of the rotating body 30 is engaged with the outer case guide 10b of the outer case 10, the rotating body 30 rotates without moving in the axial direction with respect to the outer case 10.

At this moment, at the inner case 20, the first boss 21a is restricted by the first boss receiving groove 10a of the outer case 10 from moving in the rotational direction.

Figure 7C:
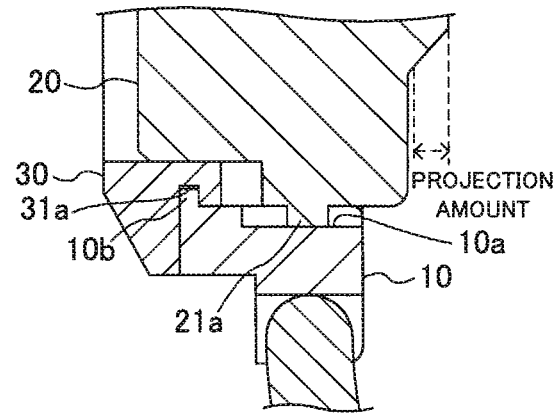
FIG. 7C is a fragmentary sectional view showing a change of an engaging relationship between members schematically and a view showing a fragment of a cross-sectional view along the line A-A' in a case of an inner case being located at a back face side.
Figure 7B:
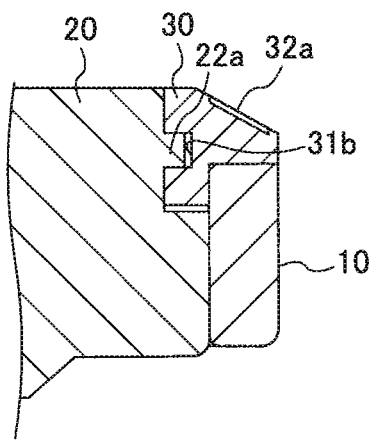
FIG. 7B is a fragmentary sectional view showing a change of an engaging relationship between members schematically and a view showing a fragment of a cross-sectional view along the line B-B' in a case of an inner case being located at a front elevation side.

Along with the abovementioned restriction, as shown in FIG. 7B, the second boss 22a becomes engaged with the second boss receiving groove 31b of the rotating body 30 and moves to the terminal position.

In other words, the inner case 20 is moved to the front elevation side by the rotating body 30 and enters the state shown in FIG. 6A.

Furthermore, in the case of the rotating body 30 being rotated right when viewed from the front, as shown in FIG. 7C, since the rotating body guide groove 31a of the rotating body 30 is engaged with the outer case guide 10b of the outer case 10, the rotating body 30 rotates without moving in the axial direction with respect to the outer case 10.

At this moment, at the inner case 20, the first boss 21a is restricted by the first boss receiving groove 10a of the outer case 10 from moving in the rotational direction.

Figure 7D:
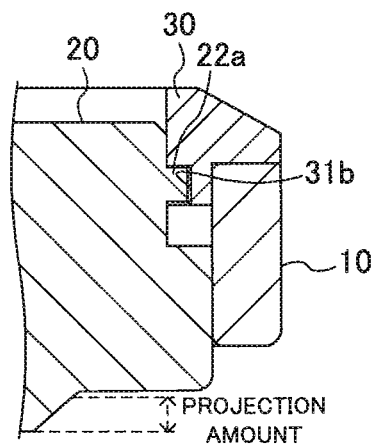
FIG. 7D is a fragmentary sectional view showing a change of an engaging relationship between members schematically and a view showing a fragment of a cross-sectional view along the line B-B' in a case of an inner case being located at a back face side.

Along with the abovementioned restriction, as shown in FIG. 7D, the second boss 22a becomes engaged with the second boss receiving groove 31b of the rotating body 30 and moves to the bending point.

In other words, the inner case 20 is moved to the back face side by the rotating body 30 and enters the state shown in FIG. 6B.

As mentioned above, by switching between the states of FIG. 6A and FIG. 6B, the projection amount of the inner case 20 changes, as shown in FIG. 7.

By rotating the rotating body 30, it is possible to move the inner case 20 in the upper/lower direction of the front elevation side and the back face side.

[Operation]

Next, operation of the electronic apparatus 1 will be explained.

FIG. 8 is a view showing a state during which a rotating position of the rotating body 30 at the electronic apparatus 1 has changed.

Figure 8A:
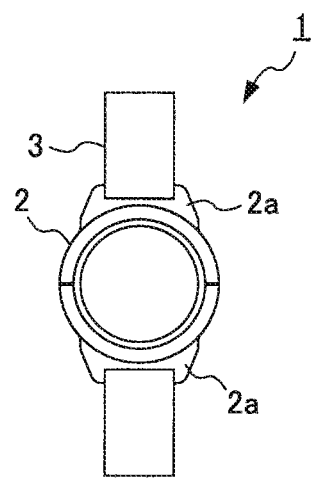
FIG. 8A is a view showing a state during which a rotating position of a rotating body at an electronic apparatus has changed, and is a front elevation view showing a structure of a case of a rotating body being rotated to the left as viewed from the front.
Figure 8B:
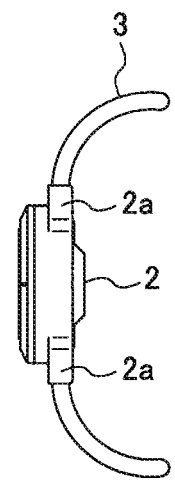
FIG. 8B is a view showing a state during which a rotating position of a rotating body at an electronic apparatus has changed, and is a front elevation view showing a structure of a case of a rotating body being rotated to the left as viewed from the front.
Figure 8C:
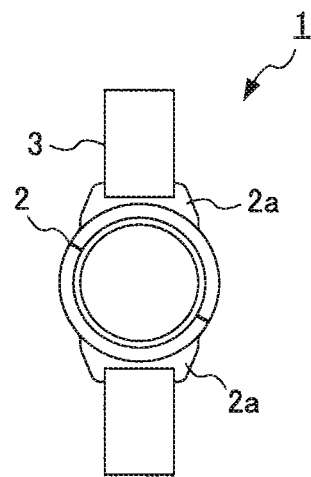
FIG. 8C is a view showing a state during which a rotating position of a rotating body at an electronic apparatus has changed, and is a front elevation view showing a structure of a case of a rotating body being rotated to the right as viewed from the front.
Figure 8D:
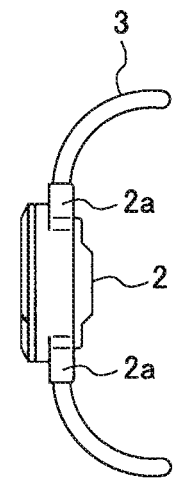
FIG. 8D is a view showing a state during which a rotating position of a rotating body at an electronic apparatus has changed, and is a front elevation view showing a structure of a case of a rotating body being rotated to the right as viewed from the front.

FIG. 8A and FIG. 8B show a case of the rotating body 30 being rotated left as viewed from the front and FIG. 8C and FIG. 8D show a case of the rotating body 30 being rotated right as viewed from the front.

The electronic apparatus 1 includes the sensor 20b at the back face side, and the sensor 20b is pressed to the living body when detecting biological information. On the one hand, since a feeling of pressure is provided to a user wearing the electronic apparatus 1 when pressing the sensor 20b to the living body constantly, the electronic apparatus 1 is worn by a user with a certain amount of slack except for when detecting biological information.

More specifically, with the electronic apparatus 1, as shown in FIGS. 8A and 8B, except for when detecting biological information, the rotating body 30 is rotated left as viewed from the front and the second boss 22a is positioned at the terminal position of the second boss receiving groove 31b, by means of which the inner case 20 is moved to the front elevation side with respect to the outer case 10.

With such a configuration, the inner case 20 enters the state of being drawn into the outer case 10, and thus the user can wear the electronic apparatus 1 with a certain amount of slack between the wrist and the electronic apparatus 1.

On the other hand, with the electronic apparatus 1, when detecting biological information, as shown in FIGS. 8C and 8D, the rotating body 30 is rotated to the right as viewed from the front, and the second boss 22a is positioned at a bending point of the second boss receiving groove 31*b*, by means of which the inner case 20 is moved to the back face side with respect to the outer case 10.

With such a configuration, the inner case 20 enters the state of projecting from the outer case 10 to the back face side, and thus the user can wear the electronic apparatus 1 in the state of the sensor 20*b* being worn under pressure to the user's wrist.

At this moment, it is possible to adjust the projection amount of the inner case 20 from the outer case 10 by way of the rotating amount of the rotating body 30.

As described above, with the electronic apparatus 1 according to the present embodiment, the inner case 20 engaging with the outer case 10 and the rotating body 30 cooperates with the rotation with respect to the outer case 10 of the rotating body 30, and thus projects from the outer case 10 and is drawn into the outer case 10.

Due to this, it is possible to press the sensor 20*b* provided at the back side (the live body side when wearing) of the inner case 20 to the living body, and release the sensor 20*b* from pressing by way of simple operations.

Therefore, it is possible to improve convenience in a wearable electronic apparatus that measures biological information.

Furthermore, it is possible to press the sensor 20*b* to the living body by rotating the rotating body 30 without contacting the inner case 20 including the sensor 20*b*.

In addition, it is possible to operate the rotating body 30 while viewing the display 20*a* provided at the front elevation side of the inner case 20.

Moreover, it is possible to flexibly set the rotation of the rotating body 30 and the projection amount of the inner case 20 according to the setting of the form of the second boss receiving groove 31*b* of the rotating body 30.

With the abovementioned configuration, the electronic apparatus 1 can be configured so as to suite a male user, female user, child user, etc.

Furthermore, since it is possible to stop the rotating position of the rotating body 30 at an arbitrary position, it is possible to adjust the projection amount of the inner case 20 appropriately according to the individual user's variations of the states of wearing the electronic apparatus 1.

Modified Example 1

In the abovementioned embodiment, as shown in FIG. 6, it is explained that the second boss receiving groove 31*b* bends at a bending point after extending in the generating line from the end of the back face side, and extends in the circumferential direction up to the terminal position located in the middle of the inner circumferential face as approaching the end of the front elevation side, at the inner circumferential face of the inner cylindrical part 31.

In contrast, the second boss receiving groove 31*b* may be differently configured so long as the inner case 20 is moved in the axial direction by being cooperated with the rotation of the rotating body 30.

Figure 9:
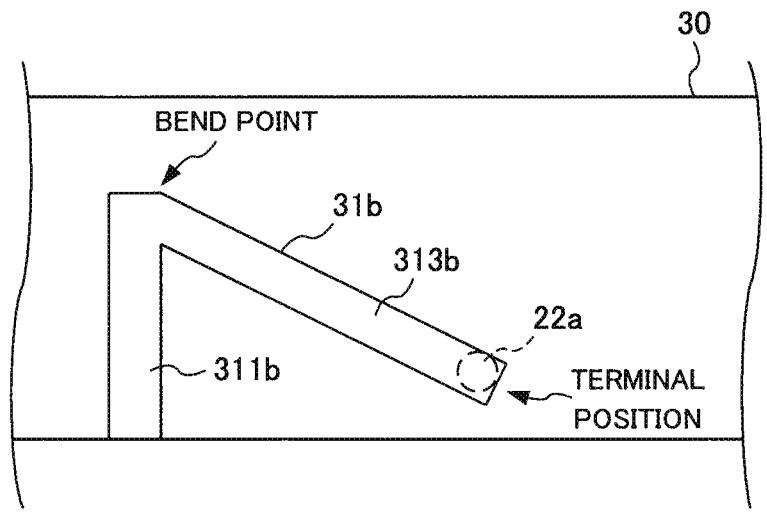
FIG. 9 is a schematic view showing another configuration example of a second boss receiving groove.

FIG. 9 is a schematic view showing another configuration example of the second boss receiving groove 31*b*.

As shown in FIG. 9, the second boss receiving groove 31*b* can be configured to include the straight part 311*b* that extends from the end of the back face side to the bending point in the direction of the generating line at the inner circumferential face of the inner cylindrical part 31 and the oblique part 313*b* that is bent from the straight part 311*b* and extends in the circumferential direction up to the terminal position in the middle of the inner circumferential face as approaching the end on the back face side.

In the case of the abovementioned configuration, contrary to the configuration of FIG. 6, when the rotating body 30 is rotated to the left as viewed from the front, the inner case 20 is moved to the back face side, and when the rotating body 30 is rotated right as viewed from the front, the inner case 20 is moved to the front elevation side.

Even in the case of such a configuration, it is possible to press the sensor 20*b* provided at the back side (the live body side when wearing) of the inner case 20 to the living body and release the sensor 20*b* from pressing by way of simple operations.

Therefore, it is possible to improve convenience in a wearable electronic apparatus that measures biological information.

Modified Example 2

In the abovementioned embodiment, it is explained that the second boss receiving groove 31*b* is configured so that the second boss 22*a* can move continuously from the bending point to the terminal position.

In contrast, the second boss receiving groove 31*b* can be configured so as to increase the resistance at a predetermined position with respect to the movement of the second boss 22*a*.

Figure 10:
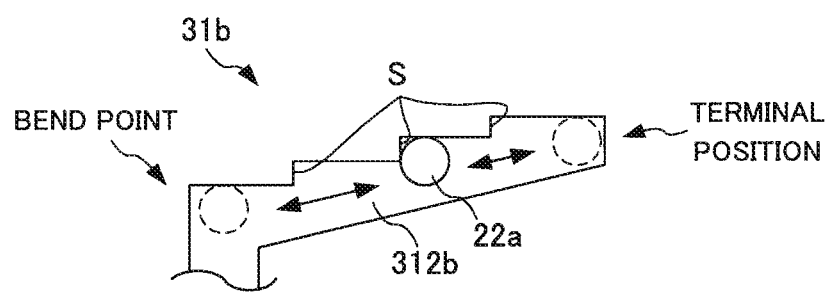
FIG. 10 is a schematic view showing a configuration example in which steps are provided so as to increase resistance with respect to movement of a second boss at predetermined positions of a second boss receiving groove.

FIG. 10 is a schematic view showing a configuration example in which steps S are provided so as to increase the resistance with respect to the movement of the second boss 22*a* at predetermined positions of the second boss receiving groove 31*b*.

In the configuration shown in FIG. 10, a predetermined number of steps S are provided at the lateral side of the second boss receiving groove 31*b*. The height of the steps S is set to less than the radius of the second boss 22*a*.

It is configured so that the second boss 22*a* overcomes the steps S in a case of the second boss 22*a* being pushed to the step S by the rotating body 30 being rotated.

In the case with such a configuration, when the second boss 22*a* moves within the second boss receiving groove 31*b*, since a certain resistance is imparted at the steps S, it is possible to cause the rotation of the rotating body 30 to stop easily at the positions of the step S.

In other words, at a position corresponding to the step S of the second boss receiving groove 31*b*, it is possible to easily stop the movement in the axial direction in the inner case 20 and it is possible to set steps for the extent to which the electronic apparatus 1 is pressed to the living body.

It should be noted that, although the example in which the steps S are provided at the one lateral side of the second boss receiving groove 31*b* is shown in FIG. 10, it may be configured to provide the steps S at both lateral sides of the second boss receiving groove 31*b*, respectively.

In such a case, it is possible to easily stop the rotation of the rotating body 30 at the position of the step S even in a case of rotating the rotating body 30 in either rotational direction.

Modified Example 3

In the abovementioned embodiment, it is explained that the second boss 22*a* is directly in contact with the lateral side of the second boss receiving groove 31*b*, and the second boss 22*a* in the second boss receiving groove 31*b* can be slid continuously from the bending point to the terminal position.

On the other hand, it is also possible to install a bearing and an elastic bod (coil spring, etc.) between the second boss 22a and the second boss receiving groove 31b so as to bias the bearing by way of the elastic body to the side of the second boss receiving groove 31b.

Then, it is possible to improve the resistance at a certain position with respect to the movement of the second boss 22a by installing a recessed part to which a part of the bearing is fit at a predetermined location at the lateral side of the second boss receiving groove 31b.

Figure 11:
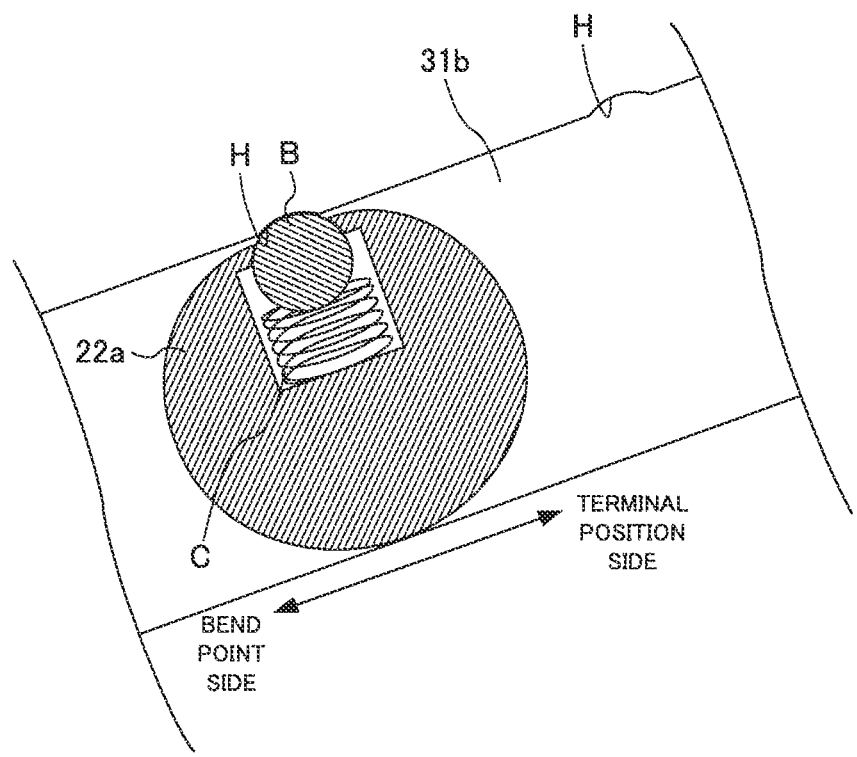
FIG. 11 is a schematic view showing a configuration having a recessed part at a lateral side of a second boss receiving groove by setting a bearing and an elastic body between a second boss and a second boss receiving groove.

FIG. 11 is a schematic view showing a configuration having a recessed part at the lateral side of the second boss receiving groove 31b by setting a bearing B and an elastic body C between the second boss 22a and the second boss receiving groove 31b.

In the configuration shown in FIG. 11, the bearing B is retained in a rotatable manner in the second boss 22a, and the bearing B is biased to the side of the second boss receiving groove 31b.

Furthermore, a predetermined number of the recessed parts H fit to a part of the bearing B are provided at the lateral side of the second boss receiving groove 31b.

In the case of such a configuration, when the second boss 22a moves within the second boss receiving groove 31b, since a certain resistance is imparted by the bearing B being fit to the recessed part H, it is possible to cause the rotation of the rotating body 30 to stop easily at the position of the recessed part H.

Modified Example 4

In the abovementioned embodiment, it may be configured so that a projection is provided at the lateral side of the terminal position side adjacent to the bending point of the second boss receiving groove 31b, with the projection serving as the resistance to movement of the second boss 22a toward the bending point.

Figure 12:
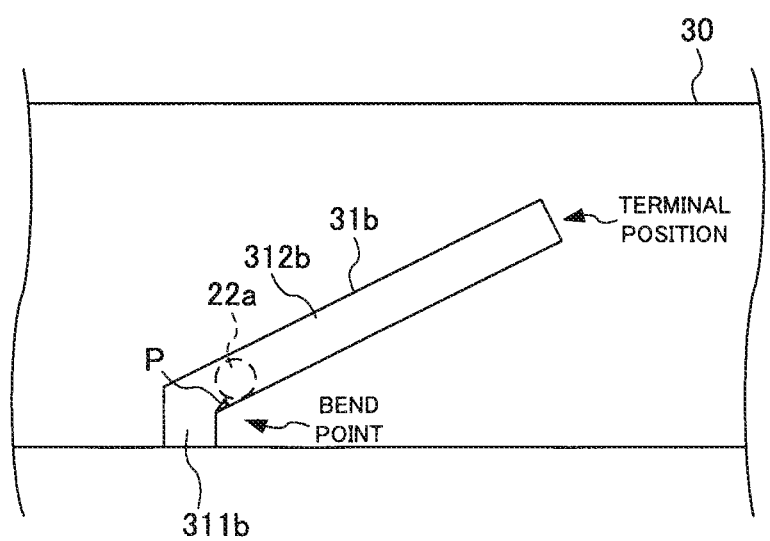
FIG. 12 is a schematic view showing a configuration example including a projection at a lateral side of a terminal position side adjacent to a bending point of a second boss receiving groove.

FIG. 12 is a schematic diagram showing a configuration example including a projection P at the lateral side of the terminal position side adjacent to the bending point of the second boss receiving groove 31b.

In the case of such a configuration, when assembling the inner case 20 to the rotating body 30, after the second boss 22a being fit to the second boss receiving groove 31b, the second boss 22a can be suppressed from returning to the bending point by being in contact with the projection P even when the second boss 22a moves to the bending point by way of the rotation of the rotating body 30.

Therefore, it can be configured so that the second boss 22a is not easily removed from the second boss receiving groove 31b.

The electronic apparatus 1 configured as above includes the outer case 10, the inner case 20, and the rotating body 30.

The outer case 10 has an inner circumferential face.

The inner case 20 is inserted into the outer case 10.

The rotating body 30 is provided so as to engage with the inner case 20 and be rotatable with respect to the outer case 10, and moves in cooperation with the rotation in the upper/lower direction of the inner case 20 along the inner circumferential face of the outer case 10.

With such a configuration, the inner case 20 engaging with the rotating body 30 works with the rotation of the rotating body 30 to the outer case 10 so that the inner case 20 projects from the outer face 10 and is drawn into the outer case 10.

Due to this, it is possible to press the sensor 20b provided at the back side (the live body side when wearing) of the inner case 20 to the living body for measuring biological information, and release the sensor 20b from pressing by way of simple operations.

Therefore, it is possible to improve convenience in a wearable electronic apparatus that measures biological information.

Furthermore, the rotating body 30 and the inner case 20 are engaged with each other by means of the second boss receiving groove 31b provided at the inner circumferential face of the rotating body 30 and the second boss 22a provided at the outer circumferential face of the inner case 20 corresponding to the inner circumferential face of the rotating body 30.

Furthermore, one of the second boss receiving groove 31b and the second bosses 22a is a convex part, and the other of the second boss receiving groove 31b and the second boss 22a include a first groove part that extends obliquely.

With such a configuration, in cooperation with the rotation of the rotating body 30, the second boss 22a moves in the first groove part (the second boss receiving groove 31b), and thus it is possible to move the inner case 20 along the central axis to the front elevation side or the back face side.

Furthermore, the first groove part (the second boss receiving groove 31b) includes a straight part that extends linearly from the end of the rotating body 30 or the inner case 20 to the bending point, and the oblique part that intersects with the straight line from the bending point and extends to an end opposite to the end.

With such a configuration, when the rotating body 30 rotates and the second boss 22a is moved in the oblique part from the bending point, it is possible to move the inner case 20 in a direction of the inner case 20 being drawn into the rotating body 30.

Furthermore, the first groove part (the second boss receiving groove 31b) includes the straight part that extends linearly from the end of the rotating body 30 or the inner case 20 to the bending portion, and the oblique part that intersects with the straight part from the bending point and extends to the end.

With such a configuration, when the rotating body 30 rotates and the second boss 22a is moved in the oblique part from the bending point, it is possible that the inner case 20 is moved in a direction of being pushed out from the rotating body 30.

Furthermore, the first groove part (the second boss receiving groove 31b) includes a locking part (step S).

With such a configuration, it is possible to easily stop the movement in the axial direction in the inner case 20 at a position corresponding to the locking part.

Furthermore, the bearing B (projection) which is biased toward the groove part side by the elastic body C is provided between the second boss receiving groove 31b and the convex part of the second boss 22a (second boss 22a) and the first groove part (second boss receiving groove 31b).

Furthermore, the recessed part H to which a part of the bearing B is fit is provided at the first groove part.

With such a configuration, when the second boss 22a moves in the second boss receiving groove 31b, since a predetermined resistance is imparted by the bearing B being fit to the recessed part H, it is possible to cause the rotation of the rotating body 30 to stop easily at the position of the recessed part H.

Furthermore, the outer case 10 and the inner case 20 are engaged with each other by means of the outer case guide 10b provided at the inner circumferential face of the outer case 10 and the first boss 21a provided at the outer circumferential face of the inner case 20 corresponding to the inner circumferential face of the outer case 10.

Furthermore, one of the outer case guide 10b and the first bosses 21a is a convex part, and the other of the outer case guide 10b and the first boss 21a is a groove part (first boss receiving groove 10a) extending linearly along a face, and the one of the outer case guide 10b and the convex part of the first boss 21a moves in the upper/lower direction in the second groove part.

With such a configuration, it is possible to move in the axial direction without causing the inner case 20 to rotate with respect to the outer case 10.

Furthermore, the rotating body 30 includes the inner cylindrical part 31 having an outer circumferential face corresponding to the inner circumferential face of the outer case 10.

In addition, the rotating body 30 and the outer case 10 are engaged with each other by means of the rotating body guide groove 31a provided at the inner cylindrical part 31 and the outer case guide 10b provided to the outer case 10.

Moreover, one of the rotating guide groove 31a and the outer case guides 10b is a convex part that project from a face provided, and the other of the rotating body guide groove 31a and the outer face guide 10b includes the third groove part that extends in a circumferential direction at the face provided.

With such a configuration, even when the rotating body 30 rotates, it is possible to engage the rotating body 30 with the outer case 10 without moving the outer case 10 in the axial direction.

Furthermore, the inner case 20 includes the sensor 20b that detects biological information.

With such a configuration, by rotating the rotating body 30, it is possible to adjust the extent to which the sensor 20b provided in the inner case 20 is pressed to the living body.

It should be noted that, although it is configured in the abovementioned embodiment so that the first boss 21a and the second boss 22a, which are convex parts, are provided at the inner case 20 and the first boss receiving groove 10a and the second boss receiving groove 31b, which are groove parts, are provided at the outer case 10 and the rotating body 30, it may be configured so that the convex parts and the groove parts are provided conversely.

In other words, it may be configured so that grooves corresponding to the first boss receiving groove 10a and the second boss receiving groove 31b are provided at the inner case 20 and convex parts corresponding to the first boss 21a and the second boss 22a are provided at the outer case 10 and the rotating body 30.

In this case as well, similarly to the abovementioned embodiment, it is possible to realize the function whereby the inner case 20 engaging with the outer case 10 and the rotating body 30 works with the rotation of the rotating body 30 to the outer case 10 so that the inner case 20 projects from the outer face 10 and is drawn into the outer case 10.

Furthermore, in order to prevent the second boss 22a from being removed from the second boss receiving groove 31b, it may be configured so that a pin is provided to restrict the rotation range of the rotating body 30 with respect to the outer case 10 after assembling the outer case 10, the inner case 20, and the rotating body 30.

In this case, a guide hole that extends in a circumferential direction at the lateral side of the outer case 10 is established so as to correspond to the rotating range of the inner case 20.

Then, by fixing the pin to the rotating body 30 through the guide hole from the outside of the outer case 10, it is possible to restrict the rotation range of the pin to the range of the guide hole.

Furthermore, it may be configured so as to further include a drive unit such as a motor in the configuration of the abovementioned embodiment so that the inner case 20 is moved in the upper/lower direction along the inner circumferential face of the outer case 10 by driving the drive unit to rotate the rotating body 30.

With such a configuration, it is possible to automatically adjust the degree of pressing to the living body. Furthermore, on this occasion, it may be configured to drive the drive unit according to the timing of starting measurement so as to press to the living body only when measuring.

Second Embodiment

[Configuration]

FIG. 13 is a schematic view illustrating a back side of an electronic apparatus 1 according to the second embodiment.

Similarly to the electronic apparatus 1 of the abovementioned first embodiment, the electronic apparatus 1 according to the present embodiment is configured as a wrist-type electronic apparatus worn on a wrist, for example, and the electronic apparatus 1 includes a main body 2 and a band 3.

It should be noted that, in the electronic apparatus 1 according to the present embodiment, a method (hereinafter, referred to as "photoelectric artery method") is employed which measures pulse waveform (pulse wave) by irradiating light to a blood vessel in which the rate of light reflection or light absorption repeats changing cyclically according to a heartbeat or periodicity of pulsation so as to detect the change of light reflected from the blood vessel.

Figure 13A:
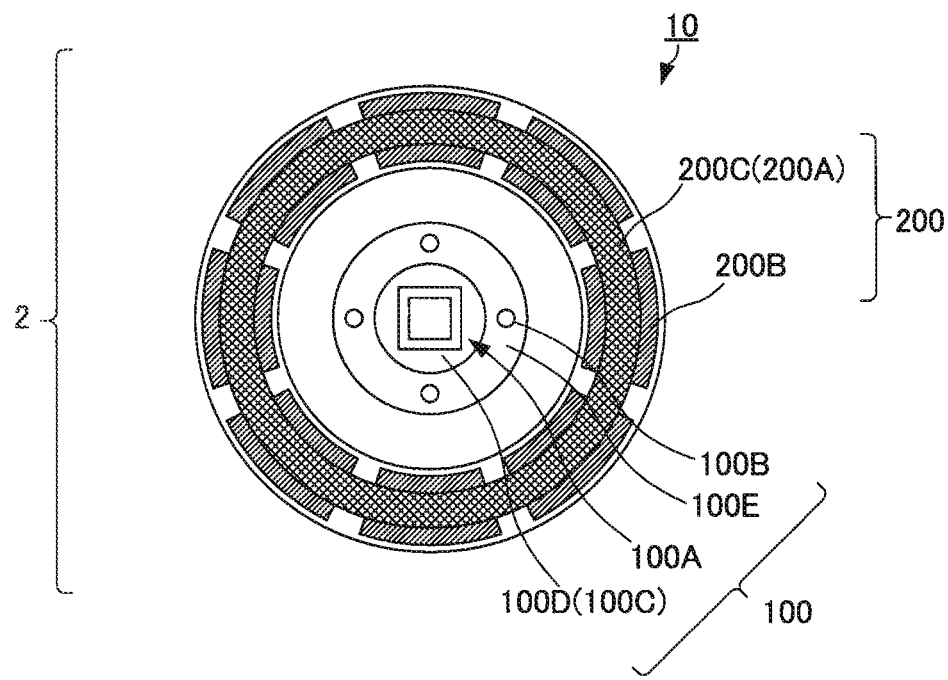
FIG. 13A is a schematic view illustrating a back side of an electronic apparatus according to the second embodiment.

As shown in FIG. 13A, when the main body 2 is viewed from the back side, the electronic apparatus 1 according to the present embodiment is provided with a sensor mechanism 100 at a central portion of an outer case 10 and a retaining mechanism 200 therearound.

The sensor mechanism 100 is a mechanism that senses a blood flow condition in vessels at the wrist of a human body to which the sensor mechanism 100 is attached.

Furthermore, the sensor mechanism 100 consists of a light receiving sensor unit 100A at a central part and four LED (Light Emitting Diode) emitting units 100B arranged in a concentric manner so as to surround the light receiving sensor unit 100A.

The light receiving sensor unit 100A is configured so that the light which emits from the LED light emitting unit 100B and is reflected can be received.

Figure 13B:
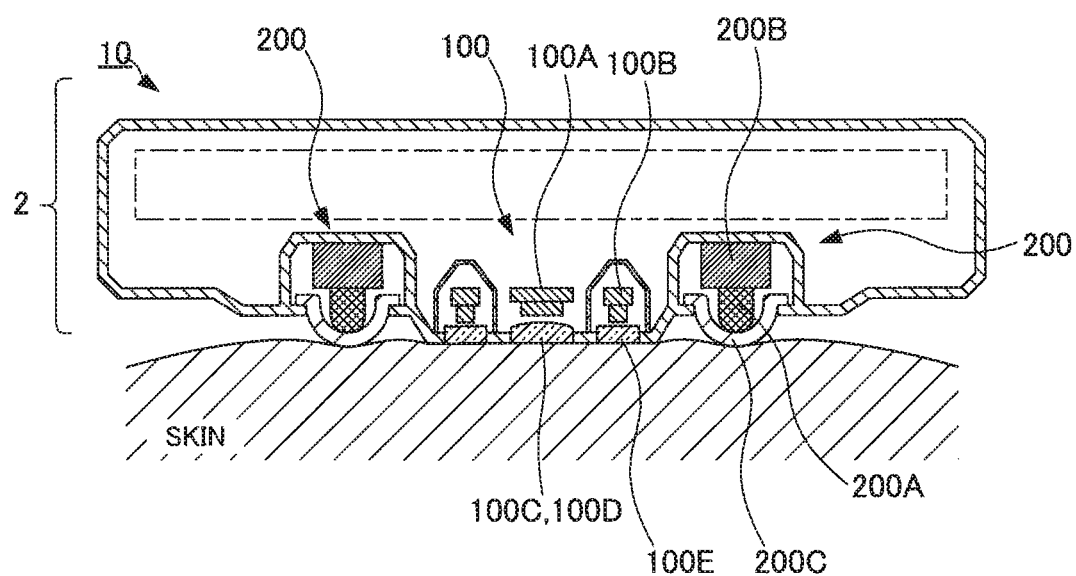
FIG. 13B is a schematic view illustrating a back side of an electronic apparatus according to the second embodiment.

As shown in FIG. 13B, a light receiving glass 100C made of a transparent glass and a lens 100D therebehind are provided at a side with which a human body is in contact (top side) of the light receiving sensor unit 100A.

The LED light emitting unit 100B is configured to be able to emit light by means of an LED, and the angle, etc. thereof is adjusted to be able to receive light at the central light receiving sensor unit 100A by the light emitted from the LED light-emitting unit 100B being reflected.

Furthermore, a cover glass 100E made of a transparent glass is provided at a side with which a human body is in contact (top side) of the LED light emitting unit 100B.

Here, the sensing method of the sensor mechanism 100 will be described.

Figure 14:
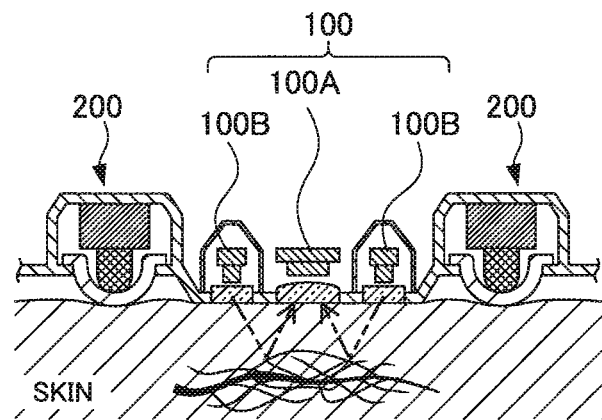
FIG. 14 is a schematic view illustrating a sensing method at a sensor mechanism.

FIG. 14 is a schematic view illustrating the sensing method of the sensor mechanism 100.

As shown in FIG. 14, the sensing method at the sensor mechanism 100 emits light from the LED light emitting unit 100B in a state of being pressed to skin so as to irradiate the light to the skin surface as a measurement target.

Thereafter, the light reflected by being incident to capillary is received through the lens by the light receiving sensor unit 100A and thus acquired as an optical signal.

The optical signal thus acquired is measured and recorded as a blood flow condition from the capillary by replacing the optical signal with an electric signal corresponding to a pulse waveform.

At the sensor mechanism 100, since the waveform of the pulsation is measured at the sensor mechanism 100, a predetermined time of period (for example, 120 seconds in the present embodiment) is set as a measured time.

It should be noted that a measured result of a blood flow condition from the capillary is output, by analyzing a measured result as, for example, the heart rate or pulse rate, stress level/relaxing level, sleepiness, sleep depth, and arterial oxygen saturation.

A retaining mechanism 200 is a mechanism for pressing to a skin between the skin and the band 3 by projecting to the wrist side and maintaining the pressed state during measurement for the purpose of preventing from being displaced from a measuring part (slip prevention) when wearing at the wrist and maintaining pressing the back side of the main body 2 to the skin.

In other words, the retaining mechanism 200 includes a retaining mechanism which operates to change the sensor mechanism 100 and the user's body between an unpress state and a press state by moving the sensor mechanism 100 at the main body 2.

As shown in FIG. 13A, the retaining mechanism 200 is formed around the whole circumference outside the sensor mechanism 100 in order to press the back side of the main body 2 evenly.

Furthermore, as illustrated in FIG. 13B, the retaining mechanism 200 consists of a pressurization foam 200A, a displacement apparatus 200B located behind the pressurization foam 200A, and a compliance cover 200C located in front of the pressurization foam 200A.

The pressurization foam 200A is a ring body of which the tip is in round shape and can press the main body 2 to the skin and release the pressed state by displacing the location.

In the present embodiment, the pressurization foam 200A is made of hard rubber, rigid plastic, or the like.

The displacement apparatus 200B is an apparatus that performs location displacement by causing the pressurization foam 200A to move in a pressing direction to protrude.

In the present embodiment, the displacement apparatus 200B is configured by a piezo actuator including layered piezo structures, and eight displacement apparatuses 200B are arranged at constant intervals in a concentric manner.

It should be noted that the number of the displacement apparatuses 200B may increase or decrease.

The compliance cover 200C is formed to cover the pressurization foam 200A from the surface side and is configured so as to be able to deal with the protrusion caused by the displacement of the location of the pressurization foam 200A and elastically deformable to be able reduce the strain on the skin.

In the present embodiment, the compliance cover 200C is made of a polymeric material such as soft rubber, resin, etc. or a material that excels in elasticity such as a fibrous material including a fabric.

Here, a pressing method of the retaining mechanism 200 to the skin will be described.

FIG. 15 is a schematic view illustrating a pressing method to the skin of the retaining mechanism 200.

Figures 15A, 15B:
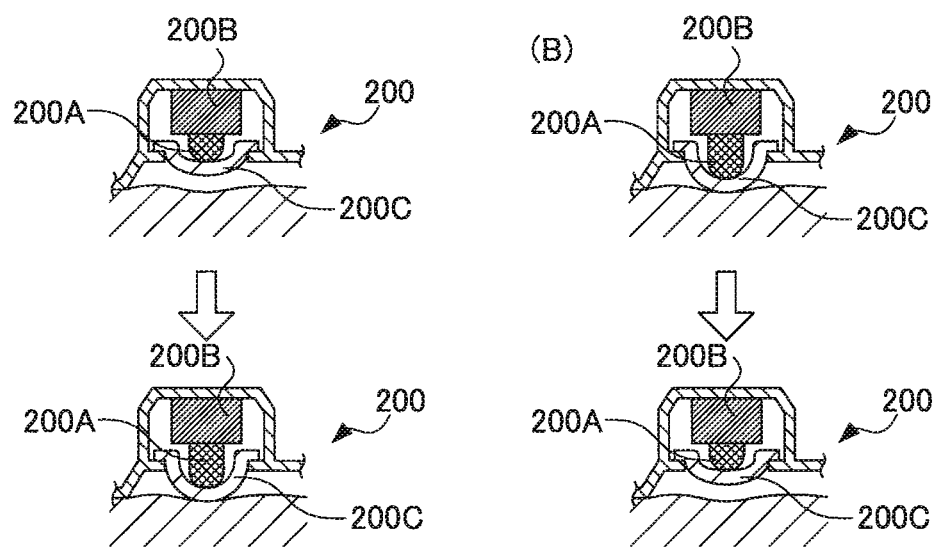
FIG. 15A is a schematic view showing a pressing method to skin at a retaining mechanism.
FIG. 15B is a schematic view showing a pressing method to skin of a retaining mechanism.

As shown in FIG. 15A, for the pressing method to the skin of the retaining mechanism 200, the displacement apparatus 200B expands to the skin side by applying a voltage to the displacement apparatus 200B during measurement, and the pressurization foam 200A is pressed down to the skin side to displace the location.

As the location of the pressurization foam 200A is displaced, the compliance cover 200C is deformed and pressed to the skin side to enter a pressed state to the skin. Furthermore, by stopping the application of voltage to the displacement apparatus 200B at the time of ending measurement, as shown in FIG. 15B, the displacement apparatus 200B expands in a direction opposite to the skin side.

By way of the abovementioned expanding/contracting operation, the pressurization foam 200A is pressed up in a direction opposite to the skin side so that the location is displaced, a result of which the compliance cover 200C is released from being pressed to the skin, and thus the pressed state to the skin is released.

In the present embodiment, it is configured so that application of the voltage at the displacement apparatus 200B is performed 10 seconds before a predetermined period of time so that it enters a pressed state at the timing of measurement.

Furthermore, it may be configured so as to provide the displacement apparatus 200B at the back side by configuring the sensor mechanism 100 to be able to move vertically with respect to the retaining mechanism 200 only to displace the sensor mechanism 100 so as to press to the user's skin.

In the electronic apparatus 1, the friction between the compliance cover 200C and the skin becomes greater due to being pressed to the skin, the positional relationship between the sensor mechanism 100 (the light receiving sensor unit 100A and the LED light emitting unit 100B) is constantly maintained even when a great vibration is applied, a result of which the measurement accuracy improves.

Furthermore, although it is also possible to perform a single measurement, measurement is performed in a predetermined interval of time in the electronic apparatus 1 according to the present embodiment.

More specifically, regarding the cycle to perform the measurement, measurement is performed over time in the interval of every 30 minutes, for example. In such a case, applying the voltage at the displacement apparatus 200B starts 10 seconds before the timing of measurement arrives, and the measurement ends when the measurement time of 120 seconds elapses.

In other words, in a case of performing measurement at the interval of every 30 minutes, it is operated so that the measurement start time (10 seconds after applying the voltage at the displacement apparatus 200B) comes 30 minutes after the measurement start time (10 seconds after applying the voltage at the displacement apparatus 200B).

[Hardware Configuration]

Figure 16:
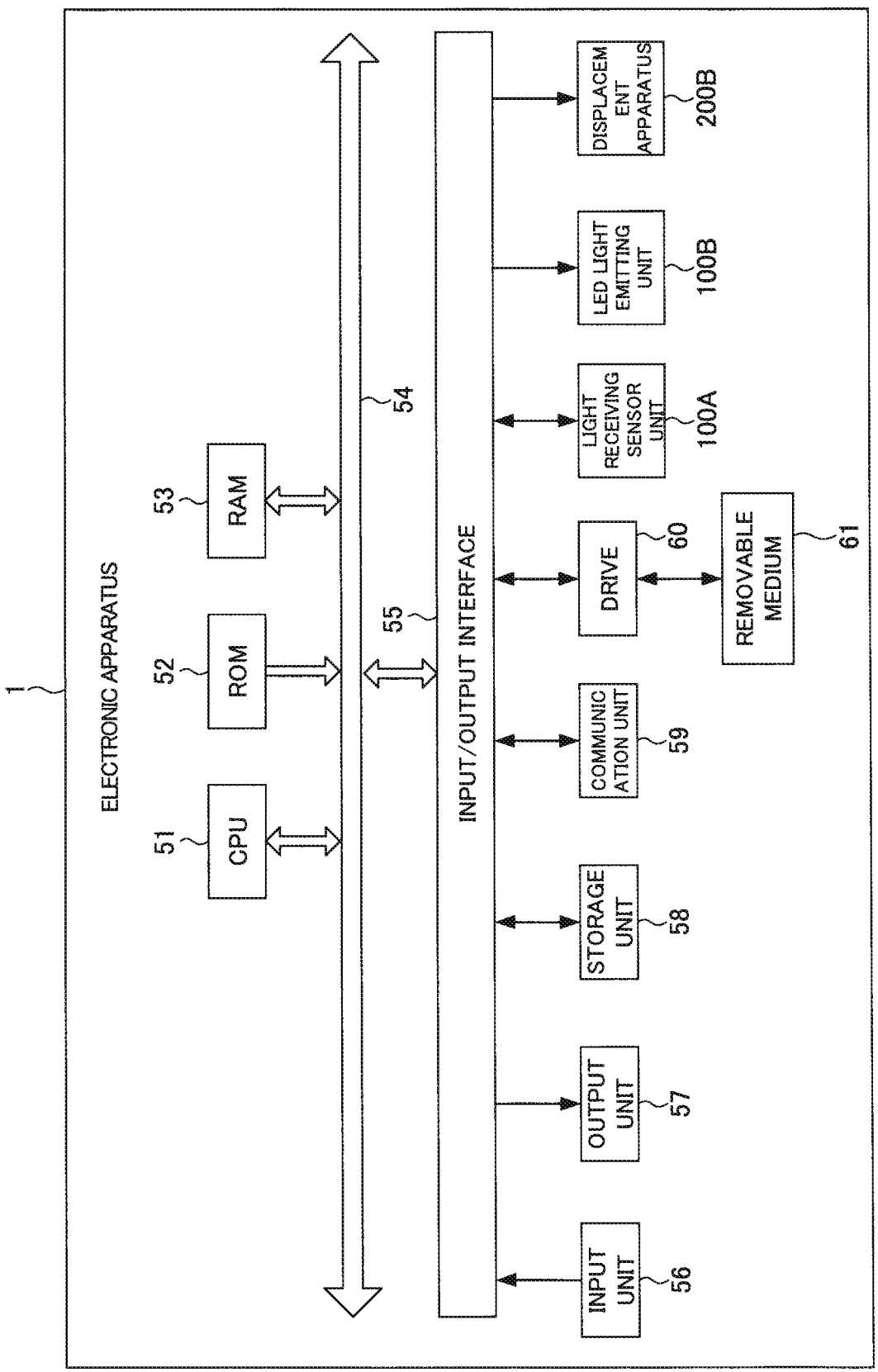
FIG. 16 is a block diagram showing a hardware configuration relating to measurement processing of an electronic apparatus according to an embodiment of the present invention.

FIG. 16 is a block diagram showing the hardware configuration relating to measurement processing of the electronic apparatus 1 according to an embodiment of the present invention.

As shown in FIG. 16, the electronic apparatus 1 includes a CPU (Central Processing Unit) 51, ROM (Read Only Memory) 52, RAM (Random Access Memory) 53, a bus 54, an input/output interface 55, an input unit 56, an output unit 57, a storage unit 58, a communication unit 59, a drive 60, an LED light emitting unit 100B, a light receiving sensor unit 100A, and a displacement apparatus 200B.

The CPU 51 executes various processing according to programs that are recorded in the ROM 52, or programs that are loaded from the storage unit 58 to the RAM 53.

The RAM 53 also stores data and the like necessary for the CPU 51 to execute the various processing, as appropriate.

The CPU 51, the ROM 52 and the RAM 53 are connected to one another via the bus 54. The input/output interface 55 is also connected to the bus 54.

The input unit 56, the output unit 57, the storage unit 58, the communication unit 59, the drive 60, the LED light emitting unit 100B, the light receiving sensor unit 100A, and the displacement apparatus 200B are connected to the input/output interface 55.

The input unit 56 is configured by various buttons and the like, and inputs a variety of information in accordance with instruction operations by the user.

The output unit 57 is configured by the display unit, a speaker, and the like, and outputs images and sound.

The storage unit 58 is configured by hard disk, DRAM (Dynamic Random Access Memory) or the like, and stores data of various images.

The communication unit 59 controls communication with other devices (not shown) via networks including the Internet.

A removable medium 61 composed of a magnetic disk, an optical disk, a magneto-optical disk, semiconductor memory or the like is installed in the drive 61, as appropriate.

Programs that are read via the drive 61 from the removable medium 61 are installed in the storage unit 58, as necessary.

Similarly to the storage unit 58, the removable medium 61 can also store a variety of data such as the image data stored in the storage unit 58.

Light emission control is performed by the CPU 51 so that the LED light emitting unit 100B irradiates light from the LED.

The light receiving sensor unit 100A converts the optical signal from the light received to electric signals corresponding to the pulsation waveform to output to the CPU 51.

At the CPU 51, the electric signals are acquired and recorded as a blood flow state from the capillary.

The displacement apparatus 200B expands and contracts by the CPU 51 performing to control displacement.

As a result, the pressurization foam 200A, etc. that performs pressing to the skin and releasing from pressing to the skin is displaced.

[Functional Configuration]

Figure 17:
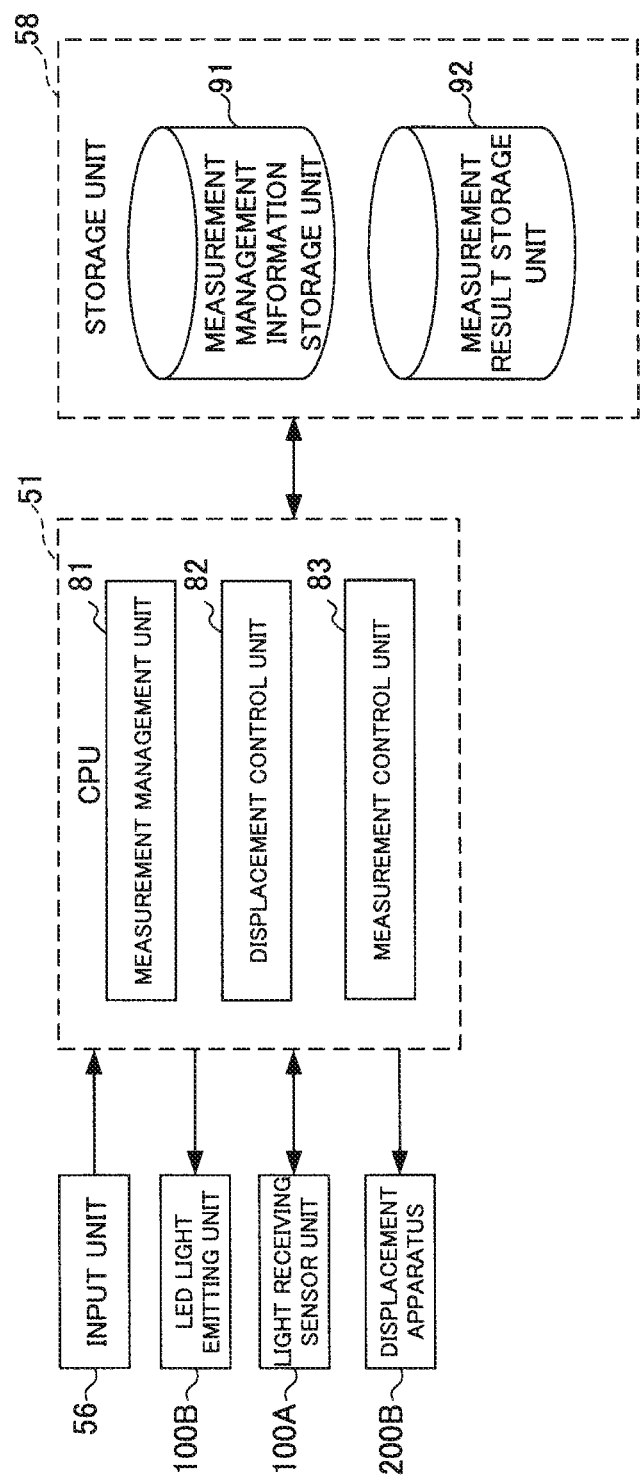
FIG. 17 is a functional block diagram showing a functional configuration for executing measurement processing among the functional configurations of an electronic apparatus of FIG. 16.

FIG. 17 is a functional block diagram showing a functional configuration for executing measurement processing, among the functional configurations of the electronic apparatus 1 of FIG. 16.

The measurement processing refers to a sequence of processing of measuring by way of light emitting/light receiving control in a predetermined period of time and controlling to press to the skin so as to establish a preferable measured state when measuring.

As shown in FIG. 17, in a case of performing the measurement processing, a measurement management unit 81, a displacement control unit 82, and a measurement control unit 83 function in the CPU 51.

Furthermore, in a region of the storage unit 58, a measurement management information storage unit 91 and a measurement result storage unit 92 are established.

In the measurement management information storage unit 91, for example, information of information serving as a trigger for performing measurement such as a measured time (hereinafter, referred to as "measurement management information") is stored.

In the measurement management storage unit 92, a measurement result of a pulsation waveform composed of the electric signals acquired is stored.

The measurement management unit 81 refers to measurement management information stored in the measurement management information storage unit 91 and manages the preparation for measuring, starting, ending, etc.

The displacement control unit 82 controls to perform applying the voltage and releasing from applying the voltage to the displacement apparatus 200B.

The measurement control unit 83 controls so as to perform emitting light and stopping emitting light at a predetermined intensity on the LED light emitting unit 100B and controls so as to perform receiving light and stopping receiving light at the light receiving sensor unit 100A.

Furthermore, the measurement control unit 83 controls the light receiving sensor unit 100A to execute a variety of signal processing such as light receiving signal conversion, which converts optical signals to electric signals.

[Operation Flow]

Figure 18:
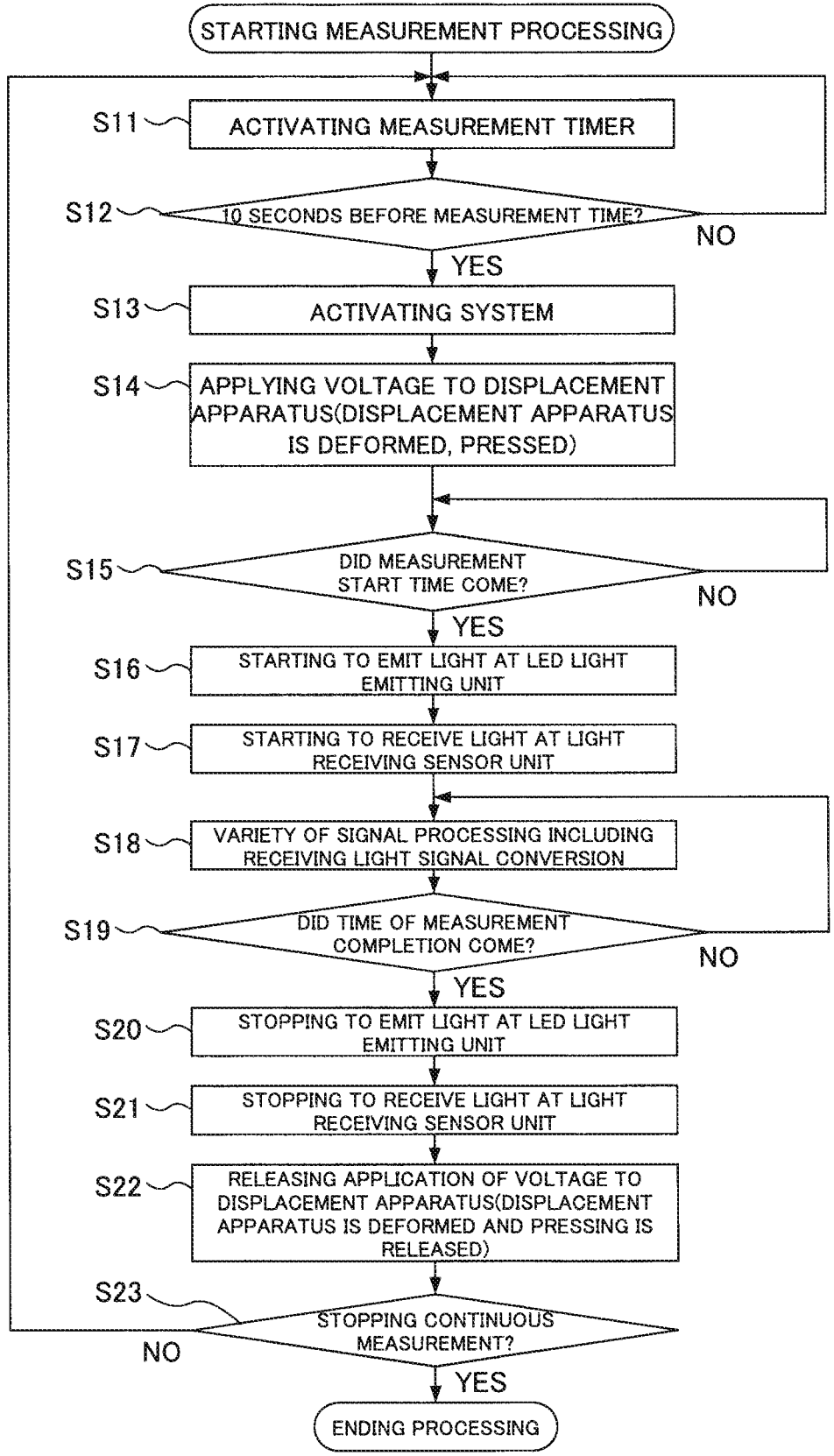
FIG. 18 is a flowchart illustrating a flow of measurement processing executed by the electronic apparatus of FIG. 16 having the functional configuration of FIG. 17.

FIG. 18 is a flowchart illustrating the flow of measurement processing executed by the electronic apparatus 1 of FIG. 16 having the functional configuration of FIG. 17.

The measurement processing starts by an operation to start the measurement processing on the input unit 56 by a user.

It should be noted that the measurement management unit 81 manages measurement timing with reference to the measurement management information stored in the measurement management information storage unit 91.

In the present embodiment, the measurement processing is managed to operate every 30 minutes for a predetermined period of time.

In Step S11, the measurement management unit 81 activates a measurement timer.

In Step S12, the measurement management unit 81 judges whether it is 10 seconds before the measurement time which is the time to apply the voltage to the displacement apparatus 200B.

If it is 10 seconds before the measurement time, it is judged as YES in Step S12, and the processing advances to Step S13.

On the other hand, if it is not 10 seconds before the measurement time, it is judged as NO in Step S12, and the processing returns to Step S11.

In Step S13, the measurement management unit 81 activates a system.

In Step S14, the displacement control unit 82 controls to apply voltage to the displacement apparatus 200B.

As a result, the displacement apparatus 200B is deformed so that the pressurization foam 200A, etc. protrudes and the main body 2 is pressed to the skin.

In Step S15, the measurement management unit 81 judges whether the measurement start time has come.

In a case in which the measurement start time has not come yet, it is judged as NO in Step S15, and the processing enters a standby state in Step S15.

On the other hand, in a case in which the measurement start time has come, it is judged as YES in Step S15, and the processing advances to Step S16.

In Step S16, the measurement control unit 83 controls the LED light emitting unit 100B to start to emit light.

In Step S17, the measurement control unit 83 controls the light receiving sensor unit 100A to start to receive light.

In Step S18, the measurement control unit 83 controls the light receiving sensor unit 100A so as to execute a variety of signal processing such as the light receiving signal conversion.

As a result, the optical signal is converted to the electric signal and a measured result of a pulsation waveform is stored in the measurement result storage unit 92.

In Step S19, the measurement management unit 81 judges whether the time of measurement completion has come.

In a case in which the time of measurement completion has come, it is judged as YES in Step S19, and the processing advances to Step S20.

On the other hand, in a case in which the time of measurement completion has not come yet, it is judged as NO in Step S19, and the processing returns to Step S18.

In Step S20, the measurement control unit 83 controls the LED light emitting unit 100B so as to stop to emit light.

In Step S21, the measurement control unit 83 controls the light receiving sensor unit 100A so as to stop to receive light.

In Step S22, the measurement control unit 83 controls to release the application of the voltage to the displacement apparatus 200B.

As a result, the displacement apparatus 200B is deformed so that the pressurization foam 200A, etc. protrudes and the main body 2 is pressed to the skin.

In Step S23, the measurement management unit 81 judges whether to stop the continuous measurement.

In a case of not stopping the continuous measurement, it is judged as NO in Step S23, and the processing returns to Step S11.

On the other hand, in a case of stopping the continuous measurement, it is judged as YES in Step S23, and the continuous measurement ends.

Such an electronic apparatus 1 is operated by identifying the timing to measure a pulsation waveform (or heart rate waveform).

It may be configured so that the measurement processing is executed automatically with a predetermined trigger or instructed by a user to be executed manually.

The electronic apparatus 1 of the present embodiment includes the retaining mechanism 200 that applies pressure to the skin as a measurement target automatically when the measurement timing comes, and press to the skin so that the positional relationship between the sensor mechanism 100 and the skin is secured and does not easily move.

The retaining mechanism 200 allows for reliable measurement of a pulsation waveform measurement.

For this reason, since the pressing of the electronic apparatus 1 is released at a time other than the time during the measurement time, operational effects are exerted in which the user does not feel irritation when wearing at a time other than the time during the measurement time and a risk for getting perspiration, getting a rash, etc. is reduced.

Therefore, it is possible to improve convenience with the electronic apparatus 1.

Modified Example 1

In the abovementioned embodiment, it can be configured so that the location of the retaining mechanism 200 is changed to be located in proximity of the light receiving sensor unit 100A and the LED light emitting unit 100B.

Figure 19A:
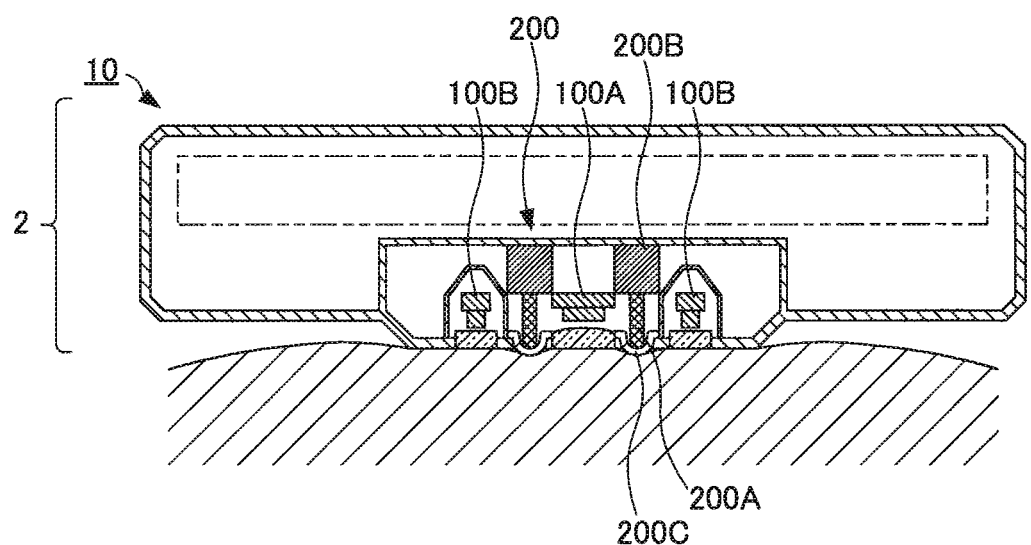
FIG. 19A is a schematic view illustrating an electronic apparatus of Modified Example 1 according to the second embodiment.
Figure 19B:
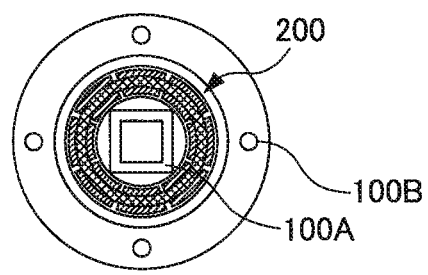
FIG. 19B is a schematic view illustrating an electronic apparatus of Modified Example 1 according to the second embodiment.

FIG. 19 is a schematic view illustrating an electronic apparatus 1 in the modified example 1 according to the second embodiment.

In the present example, as shown in FIG. 19, the retaining mechanism 200 (the pressurization foam 200A, the displacement apparatus 200B, the compliance cover 200C) is located in proximity of the light receiving sensor unit 100A inside (at the inner circumference of) the LED light emitting unit 100B.

Since the retaining mechanism 200, which is a structure to perform pressing to the skin and prevent from slipping, becomes located at a position closer to the light receiving sensor unit 100A and the LED light emitting unit 100B, there is a possibility to remove the influence of fluctuation more.

Furthermore, it is possible to anticipate an operational effect of shutting down a leaked light ray caused by light not getting through the skin from the LED light emitting unit 100B with respect to the light receiving sensor unit 100A, and thus being leaked to intrude from a space and reducing noise components of a signal, by arranging in proximity of the light receiving sensor unit 100A inside (the inner circumference of) the LED light emitting unit 100B.

Modified Example 2

In the abovementioned embodiment, it can be configured to perform an optical measurement in accordance with a pressing level by sensing a pressure when pressing.

In the present example, it is configured to provide a pressure sensor (not shown) such as a piezo sensor at the back side of the pressurization foam 200A. According to the pressure to the pressurization foam 200A, it is possible to estimate the degree of pressing to the skin.

By judging whether an optical measurement can be performed or not based on the degree of pressing to the skin, the displacement at the displacement apparatus 200B is controlled and the intensity of light emitting at the LED light emitting unit 100B is controlled.

With the abovementioned control, a notification is performed which reports to the user that an optimal measurement has not been performed or suggesting the change of the measurement location.

Figure 20D:
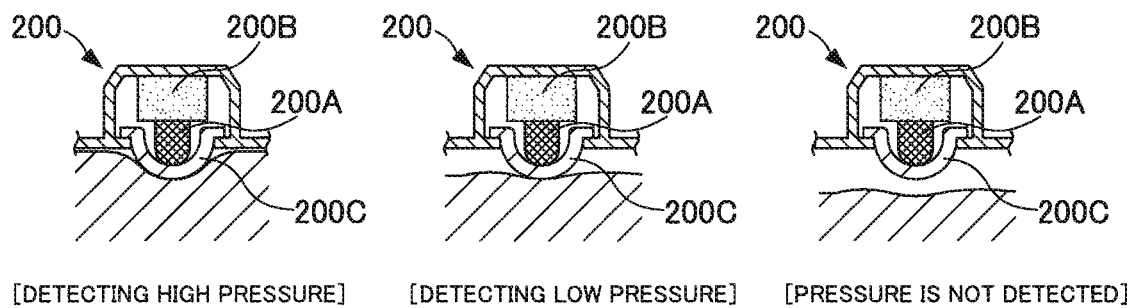
FIG. 20D is a schematic view illustrating a method of judging a pressure level.
Figure 20D:
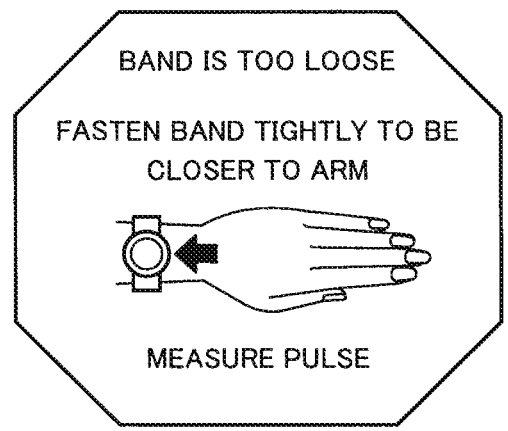

FIG. 20 is a schematic view explaining a method of judging a pressure level.

As shown in FIG. 20A, in a case in which the output of the pressure sensor is high and thus a high pressure is detected, it is judged that the pressing level is strong enough, and the measurement is performed using a standard light emitting intensity with the light emitting intensity at the LED light emitting unit 100B set at a standard intensity.

Furthermore, as shown in FIG. 20B, in a case in which the output of the pressure sensor is low and a low pressure is detected, it is judged that the pressing level is slightly low and the light emitting intensity at the LED light emitting unit 100B is made greater. In this way, it is possible to secure the measurement accuracy.

Furthermore, as shown in FIG. 20C, in a case in which there is no output from the pressure sensor (or extremely low) and the pressure is not detected (or an extremely low pressure is detected), it is judged that the pressing is extremely weak and the measurement is cancelled.

Furthermore, an alert as shown in FIG. 20D is displayed to prompt the confirmation whether to perform the measurement again. In response to the alert, the user can change a location and adjust the length of the band 3.

[Operation Flow]

Figure 21:
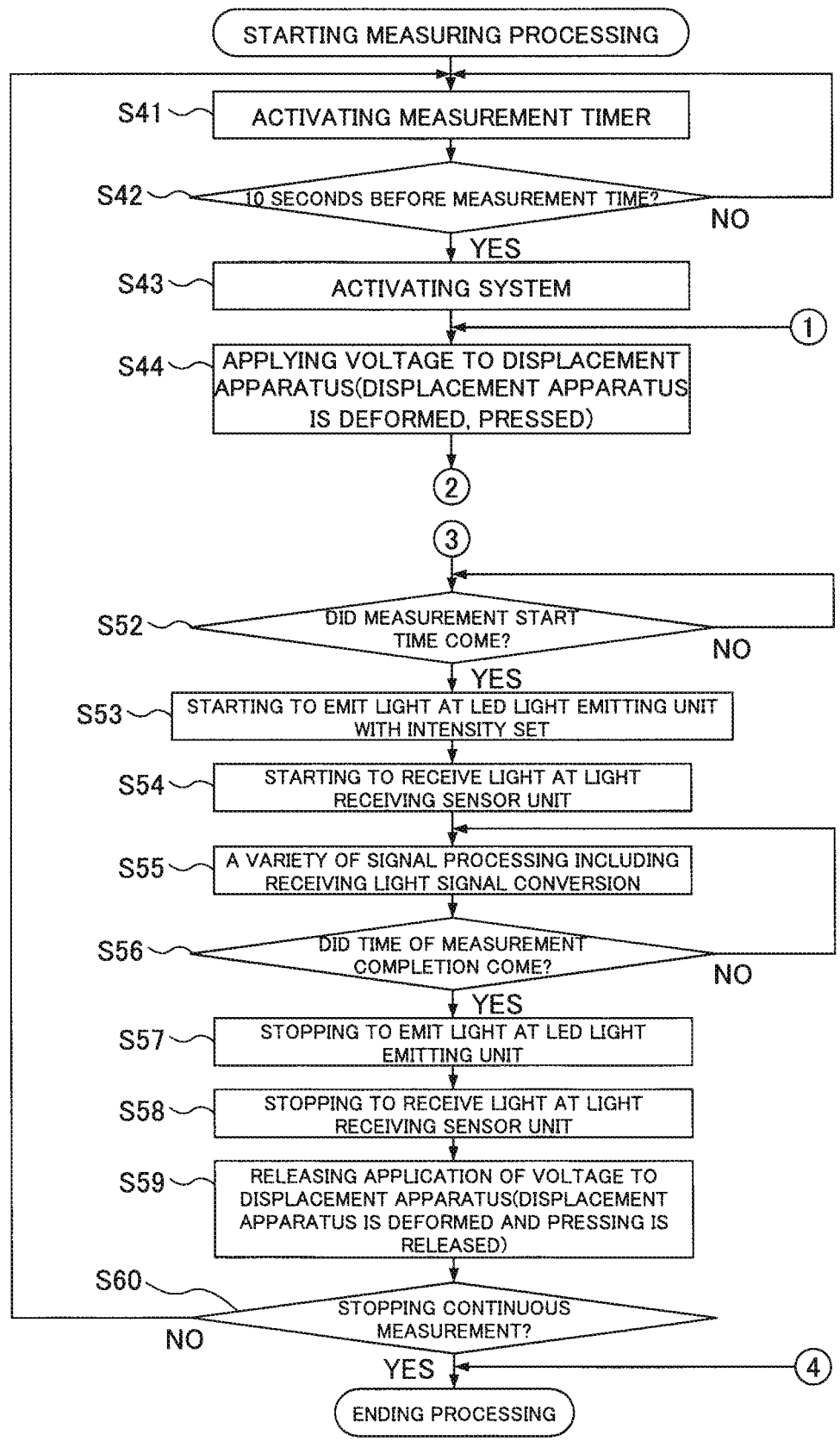
FIG. 21 is a flowchart illustrating a flow of the measurement processing in Modified Example 2.
Figure 22:
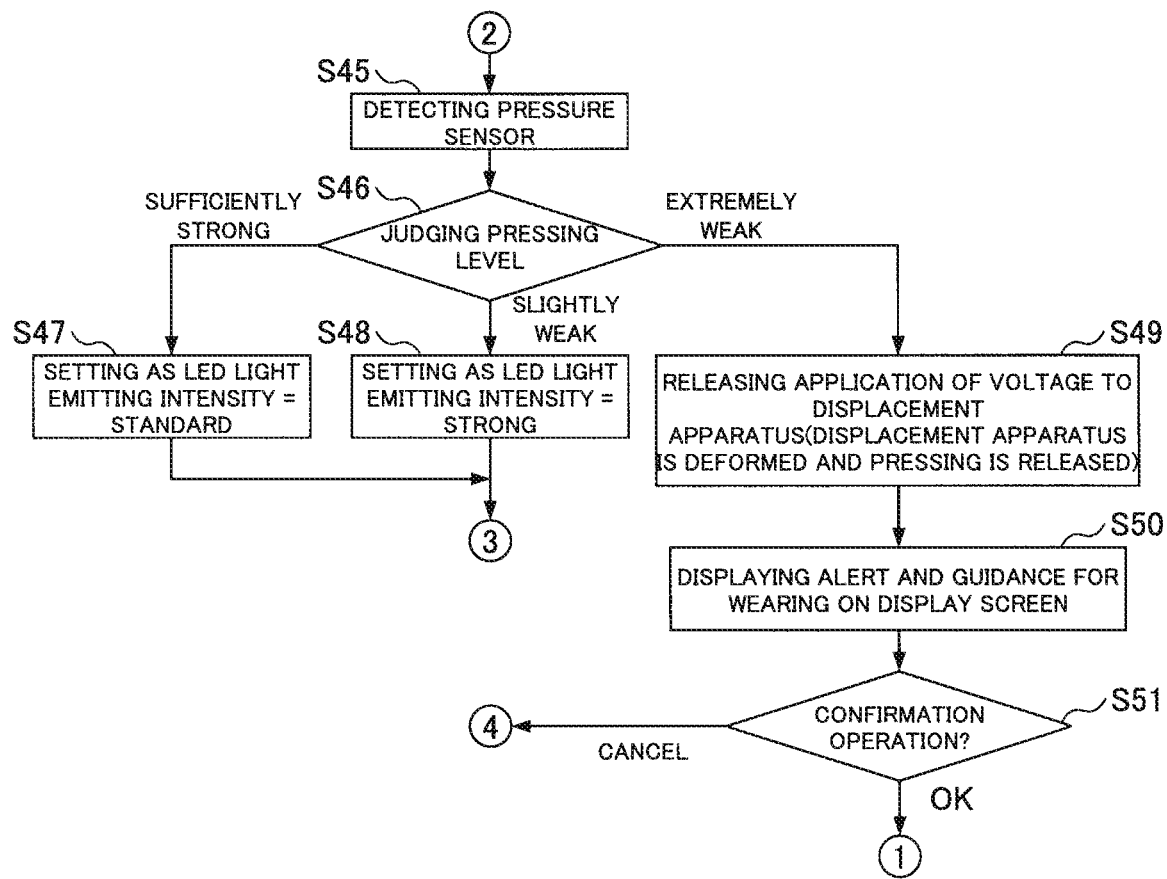
FIG. 22 is a flowchart illustrating a flow of the measurement processing in Modified Example 2.

FIGS. 21 and 22 are flowcharts illustrating a flow of the measurement processing in Modified Example 2.

It should be noted that processing similar to the first embodiment of FIG. 18 will be omitted.

In particular, since the processing of Steps S11 to Step S23 (except for Step S16), Steps S41 to S44, Step S52, and Steps S54 to S60 is identical, explanations thereof will be omitted.

In Step S45, the measurement control unit 83 controls the pressure sensor to detect a pressure.

In Step S46, the measurement control unit 83 judges a pressing level from a detected result at the pressure sensor.

In a case in which the pressing level is strong enough, it is judged as "sufficiently strong" in Step S46 and the processing advances to Step S47.

In Step S47, the measurement control unit 83 sets the LED light emitting intensity at the LED light emitting unit 100B as "standard". Then, the processing advances to Step S52.

On the other hand, in a case in which the pressing level is slightly weak, it is judged as "slightly weak" in Step S46, and the processing advances to Step S48.

In Step S48, the measurement control unit 83 sets the LED light emitting intensity at the LED light emitting unit 100B as "strong". Then, the processing advances to Step S52.

On the other hand, in a case in which the pressing level is extremely weak, it is judged as "extremely weak" in Step S46, and the processing advances to Step S49.

In Step S49, the measurement control unit 83 controls to release the application of the voltage to the displacement apparatus 200B.

As a result, the displacement apparatus 200B is deformed so that the pressurization foam 200A, etc. protrudes and the main body 2 is pressed to the skin.

In Step S50, the measurement management unit 81 controls the output unit 57 to display an alert and guidance for wearing.

As a result, a display as in FIG. 20D is outputted at the output unit 57.

In Step S51, the measurement management unit 81 judges a confirmation operation.

In a case of the confirmation operation being OK, it is judged as "OK" in Step S51, and the processing returns to Step S44.

On the other hand, in a case of the confirmation operation being cancel, it is judged as "cancel" in Step S51, and the measurement processing ends.

Furthermore, in Step S53, the measurement control unit 83 starts to emit light from the LED light emitting unit 100B with the intensity set.

In such an electronic apparatus 1, since a higher irradiation intensity is advantageous for reliable measurement but battery consumption becomes high, pulse wave measurement with higher light emitting intensity is performed only when it is assumed that the degree of stability upon wearing is low, and thus the signal output of a pressure sensor is low.

Therefore, in the electronic apparatus 1, it is possible to perform an operation according to a pressed state between the user and the LED light emitting unit 100B automatically while suppressing the electric consumption, a result of which the measurement can be performed at optimal conditions.

Modified Example 3

In the abovementioned embodiment, a device such as a piezo actuator as the retaining mechanism 200 (displacement apparatus 200B) is configured which is assumed to press from the side of the main body 2, as a mechanism of retaining to the skin.

However, the present invention is not limited to the abovementioned configuration and, in the present example, it may be configured to perform pressing by means of a piezo pump which inflates a bag body arranged at the side of the band 3 to perform pressing, as the retaining mechanism 200'.

Figure 23:
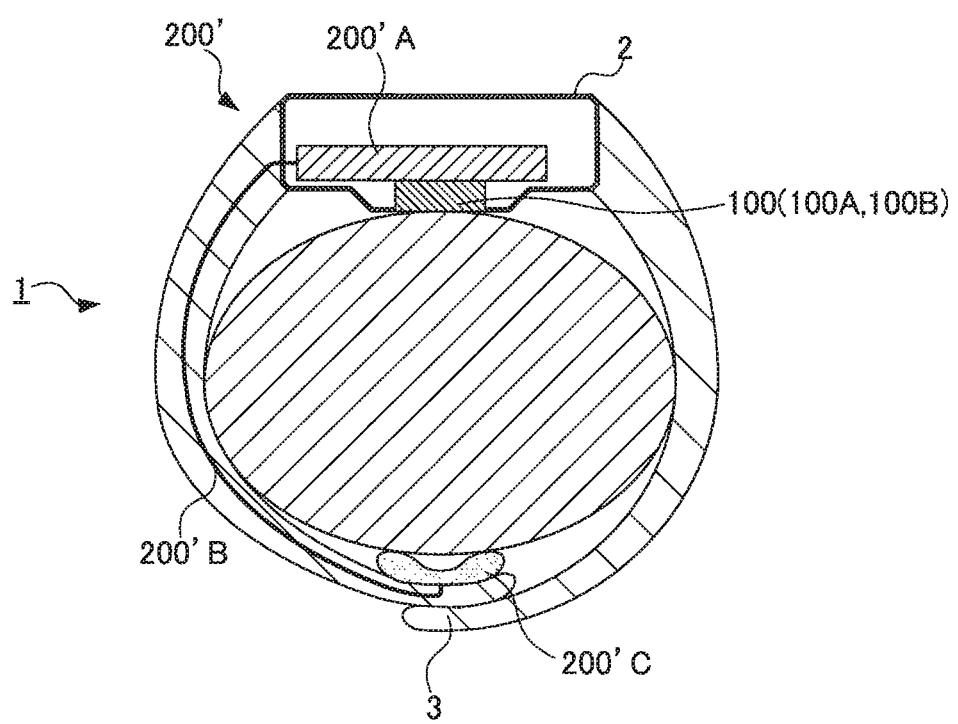
FIG. 23 is a schematic view illustrating a retaining mechanism of Modified Example 3.

FIG. 23 is a schematic view illustrating a retaining mechanism of Modified Example 3.

As shown in FIG. 23, the retaining mechanism 200' includes a micro pump main body 200'A, a pipe body 200'B, and a contraction bag 200'C.

With the retaining mechanism 200 configured as above, when the measurement start time comes, the micro pump main body 200'A operates and a fluid (or air) is sent to the contraction bag 200'C provided at the side of the band 3 opposite to the main body 2 via the pipe body 200'B to expand the contraction bag 200'C so that the sensor mechanism 100 (the light receiving sensor unit 100A and the LED light emitting unit 100B) can be pressed to the skin.

Since photoelectric artery method is employed, the electronic apparatus 1 of the present embodiment is vulnerable to fluctuation, displacement upon wearing, etc.

For this reason, to say nothing of severe exercise, every time a slight fluctuation causes the optical axis to be displaced, the alignment (positional relationship) between capillary and the light emitting element/light receiving element is ruined, a result of which the waveform is disturbed greatly.

Furthermore, once the signal is disturbed, it takes several seconds to return to a judgment with a stable periodicity.

For this reason, in a case of employing the photoelectric artery method, restrictions in use arise which include the assumption that the band 3 is fastened tightly and a person lies quietly upon measuring, for example.

For example, in a base of a band-type product, the measurement becomes stable generally by fastening tightly. However, a user may feel irritation if the product is fastened tightly at all times and other problems such as getting perspiration or getting a rash arise.

However, in the electronic apparatus 1 according to the present embodiment, a stable measurement is realized by increasing the degree of pressing between a mechanical sensor and the skin only during "the time to execute measurement". Furthermore, a user's feeling while wearing is improved by loosening the pressed state during a non-measurement time. Then, by measuring by means of a sensor relating to measurement stability and a pressure sensor which measures the degree of pressing to the skin, the measuring means can be changed so that the measurement stability in a case in which the degree of pressing is insufficient is improved.

It should be noted that, in the abovementioned embodiment, although it is configured to change a pressed state to a body of a user by way of the retaining mechanism 200, it may also be configured to include a retaining function by providing a mechanism similar to the retaining mechanism 200 to the sensor mechanism 100 itself (the light receiving sensor unit 100A and/or the LED light emitting unit 100B) without using the retaining mechanism 200 so as to be able to protrude.

Furthermore, it may also be configured with the retaining mechanism 200 and the sensor mechanism 100 (the light receiving sensor unit 100A and/or the LED light emitting unit 100B) including a retaining function.

The electronic apparatus 1 configured as above includes the sensor mechanism 100, the main body 2, and the retaining mechanism 200.

The sensor mechanism 100 acquires biological information of a user.

The main body 2 supports the sensor mechanism 100 in a movable manner in the upper/lower direction.

The retaining mechanism 200 changes between an unpress state and a press state of the sensor mechanism 100 and the user's body by moving the sensor mechanism 100 at the main body 2.

With the electronic apparatus 1, since the displacement of the sensor mechanism 100 from a body is prevented and the maintenance of the contact condition is secured, an optical measurement becomes possible, and it is thereby possible to improve convenience for a user without adjusting a position, etc.

The electronic apparatus 1 includes the displacement control unit 82 that controls the retaining mechanism 200.

The displacement control unit 82 changes a pressed state to the user's body by controlling the retaining mechanism 200.

With such a configuration, in the electronic apparatus 1, since the pressed state to the user's body can be changed, it is possible to perform the measurement at optical conditions.

The retaining mechanism 200 further includes the pressurization foam 200A that expands and contracts.

The pressurization foam 200A changes the pressed state by changing the location of the sensor mechanism 100 by way of an expanding/contracting operation.

With such a configuration, in the electronic apparatus 1, it is possible to change the pressed state to the user's body easily by way of the expanding/contracting operation.

The retaining mechanism 200 includes the pressure sensor that acquires information relating to a pressed state between the sensor mechanism 100 and the user's body.

With the electronic apparatus 1, since it is possible to judge a state according to the pressed state, it is thereby possible to improve the user's convenience.

The displacement control unit 82 controls the retaining mechanism 200 based on the information relating to the pressed state acquired by the retaining mechanism 200.

With the electronic apparatus 1, since it is possible to judge the state according to the pressed state and change the pressed state to the user's body automatically, it is thereby possible to improve the user's convenience.

The electronic apparatus 1 further includes the measurement control unit 83 that controls the measurement intensity of biological information by the sensor mechanism 100 based on the information relating to the pressed state acquired by the pressure sensor.

With the electronic apparatus 1, since it is possible to perform sensing according to a pressed state between the sensor mechanism 100 and the user's body, it is thereby possible to perform the measurement with an optimal condition.

The sensor mechanism 100 includes the LED light emitting unit 100B for measuring biological information.

The measurement control unit 83 controls the light emitting intensity of the LED light emitting unit 100B based on the information acquired by the pressure sensor.

With the electronic apparatus 1, since it is possible to change the light emitting intensity according to the pressed state between the sensor mechanism 100 and the user's body, it is thereby possible to perform the measurement with an optimal condition.

The displacement control unit 82 controls the retaining mechanism 200 at a predetermined interval of time.

With the electronic apparatus 1, for example, since the retaining mechanism 200 is controlled every interval of time of the measurement, it is thereby possible to perform the measurement with an optimal condition.

It should be noted that the present invention is not to be limited to the aforementioned embodiments, and that modifications, improvements, etc. within a scope that can achieve the objects of the present invention are also included in the present invention.

In the aforementioned embodiments, explanations are provided with the example of the electronic apparatus 1 to which the present invention is applied being a wrist-type electronic apparatus mounted on a wrist; however, the present invention is not limited thereto in particular.

For example, the present invention can be applied to any electronic device mounted on a body part other than a wrist (for example, an upper arm). In other words, the present invention can be applied to a variety of kinds of wearable electronic apparatuses.

The processing sequence described above can be executed by hardware, and can also be executed by software.

In other words, the hardware configuration of FIG. 17 is merely an illustrative example, and the present invention is not particularly limited thereto. More specifically, the types of functional blocks employed to realize the above-described functions are not particularly limited to the example shown in FIG. 17, so long as the e apparatus 1 can be provided with the functions enabling the aforementioned processing sequence to be executed in its entirety.

A single functional block may be configured by a single piece of hardware, a single installation of software, or a combination thereof.

In a case in which the processing sequence is executed by software, the program configuring the software is installed from a network or a storage medium into a computer or the like.

The computer may be a computer embedded in dedicated hardware. Alternatively, the computer may be a computer capable of executing various functions by installing various programs, e.g., a general-purpose personal computer.

The storage medium containing such a program can not only be constituted by the removable medium 61 of FIG. 16 distributed separately from the device main body for supplying the program to a user, but also can be constituted by a storage medium or the like supplied to the user in a state incorporated in the device main body in advance. The removable medium 61 is composed of, for example, a magnetic disk (including a floppy disk), an optical disk, a magnetic optical disk, or the like. The optical disk is composed of, for example, a CD-ROM (Compact Disk-Read Only Memory), a DVD (Digital Versatile Disk), Blu-ray (Registered Trademark) or the like. The magnetic optical disk is composed of an MD (Mini-Disk) or the like. The storage medium supplied to the user in a state incorporated in the device main body in advance is constituted by, for example, the ROM 52 of FIG. 16 in which the program is recorded or the hard disk, etc. included in the storage unit 58 of FIG. 16.

It should be noted that, in the present specification, the steps defining the program recorded in the storage medium include not only the processing executed in a time series following this order, but also processing executed in parallel or individually, which is not necessarily executed in a time series.

The embodiments of the present invention described above are only illustrative, and are not to limit the technical scope of the present invention. The present invention can assume various other embodiments. Additionally, it is possible to make various modifications thereto such as omissions or replacements within a scope not departing from the spirit of the present invention. These embodiments or modifications thereof are within the scope and the spirit of the invention described in the present specification, and within the scope of the invention recited in the claims and equivalents thereof.

What is claimed is:
1. An electronic apparatus comprising:
a sensor unit that acquires biological information of a user;
an outer case that has an inner circumferential face which supports the sensor unit in a movable manner in a direction perpendicular to a pressing surface;
an inner case which is inserted into the outer case and has the sensor unit; and
a pressing portion that changes the sensor unit and a body of the user between an unpress state and a press state by moving the inner case in the direction supported by the inner circumferential face of the outer case.

2. The electronic apparatus according to claim 1,
further comprising a first control unit that controls the pressing portion,
wherein
the first control unit changes the pressed state to the body of the user by controlling the pressing portion.

3. The electronic apparatus according to claim 2,
wherein the pressing portion further includes an expanding/contracting member, and
wherein the expanding/contracting member changes the pressed state by changing a position of the sensor unit by way of an expanding/contracting operation.

4. The electronic apparatus according to claim 2,
wherein the pressing portion includes an information acquisition unit that acquires information relating to a pressed state between the sensor unit and the body of the user.

5. The electronic apparatus according to claim 4,
wherein the first control unit controls the pressing portion based on the information acquired by the information acquisition unit.

6. The electronic apparatus according to claim 4,
further comprising a second control unit that controls measurement intensity of biological information by the sensor unit based on the information acquired by the information acquisition unit.

7. The electronic apparatus according to claim 6,
wherein the sensor unit includes a light source unit for measuring biological information, and
wherein the second control unit controls a light emitting intensity of the light source unit based on the information acquired by the information acquisition unit.

8. The electronic apparatus according to claim 2,
wherein the first control unit controls the pressing portion at a predetermined interval of time.

9. The electronic apparatus according to claim 1,
wherein the pressing portion includes a rotating body which is provided so as to be engaged with the inner case and rotatable with respect to the outer case and operates in corporation with a rotation to move the inner case in an upper/lower direction along the inner circumferential face of the outer case.

10. The electronic apparatus according to claim 9,
wherein the rotating body and the inner case are engaged with a first rotating body side engaging portion provided at the inner circumferential face of the rotating body and a first inner case side engaging portion provided at an outer circumferential face of the inner case corresponding to the inner circumferential face of the rotating body, and
wherein one of the first rotating body side engaging portion and the first inner case side engaging portions is a convex portion, and the other of the first rotating body side engaging portion and the first inner case side engaging portion includes a first groove portion that extends obliquely.

11. The electronic apparatus according to claim 10,
wherein the first groove portion includes a straight portion that extends linearly from an end of the rotating body or the inner case to a bending point, and an oblique portion that extends to an end opposite to the end.

12. The electronic apparatus according to claim 10,
wherein the first groove portion includes a straight portion that extends linearly from an end of the rotating body or the inner case to a bending point and an oblique portion that intersects with the straight portion from the bending point and extends to the end.

13. The electronic apparatus according to claim 10,
wherein the first groove portion has a locking portion.

14. The electronic apparatus according to claim 10,
further comprising a projection portion that is biased toward a side of the first groove portion by an elastic body between the convex portions of the first rotating body side engaging portion and the first inner case side engaging portion and the first groove portion,
wherein a recessed portion to which a part of the projection portion is fit is provided at the first groove portion.

15. The electronic apparatus according to claim 9,
wherein the outer case and the inner case are engaged with each other by a first outer case side engaging portion provided at the inner circumferential face of the outer case and a second inner case side engaging portion provided at an outer circumferential face of the inner case corresponding to the inner circumferential face of the outer case, and
wherein one of the first outer case side engaging portion and the second inner case side engaging portion is a convex portion, and the other of the first outer case side engaging portion and the second inner case side engaging portion is a second groove portion that extends linearly along a face, and the one of the convex portions of the first outer case side engaging portion and the second inner case side engaging portion moves vertically in the second groove portion.

16. The electronic apparatus according to claim 9,
wherein the inner case includes a sensor that detects biological information.

17. The electronic apparatus according to claim 1,
wherein the inner case moves in the direction only perpendicular to the pressing surface.

18. The electronic apparatus according to claim 1,
wherein the outer case has an engaging portion at the inner circumferential face, the engaging portion supports the inner case in the movable manner in the direction perpendicular to the pressing surface.

19. An electronic apparatus comprising:
a sensor unit that acquires biological information of a user;
an outer case that supports the sensor unit in a movable manner in an upper/lower direction; and
a pressing portion that changes the sensor unit and a body of the user between an unpress state and a press state by moving the sensor unit, wherein the outer case has an inner circumferential face and further includes an inner case inserted into the outer case, wherein the pressing portion includes a rotating body which is provided so as to be engaged with the inner case and rotatable with respect to the outer case and operates in corporation with a rotation to move the inner case in an upper/lower direction along the inner circumferential face of the outer case, wherein the rotating body includes an inner cylindrical portion having an outer circumferential face corresponding to an inner circumferential face of the outer case, wherein the rotating body and the outer case are engaged with each other by a second rotating body side engaging portion provided at the inner cylindrical portion and a second outer case side engaging portion provided at the outer case, and wherein one of the second rotating body side engaging portion and the second outer case side engaging portions is a convex portion that projects from a face provided, and the other of the second rotating body side engaging portion and the outer case side engaging portions includes a third groove portion that extends in a circumferential direction at a face provided.

20. A method for using an electronic apparatus that includes an inner case carrying a sensor unit that acquires biological information of a user, an outer case that supports the inner case including the sensor unit in a movable manner in an upper/lower direction, and a pressing portion that changes the sensor unit and a body of the user between an unpress state and a press state by moving the sensor unit, the method for using the electronic apparatus comprising:

a control step of changing a pressed state between a body of a user and the sensor unit by controlling the pressing portion so that the inner case carrying the sensor unit is moved relative to the outer case.

21. A non-transitory storage medium encoded with a computer-readable program that enables a computer which controls an electronic apparatus including:

an inner case that carries a sensor unit that acquires biological information of a user;

an outer case that supports the inner case including the sensor unit in a movable manner in an upper/lower direction; and a pressing portion that changes the sensor unit and a body of the user between an unpress state and a press state by moving the sensor unit, to execute functions as:

a control unit that changes a pressed state between a body of a user and the sensor unit by controlling the pressing portion so that the inner case carrying the sensor unit is moved relative to the outer case.

* * * * *